United States Patent
Gress et al.

(10) Patent No.: US 6,649,744 B1
(45) Date of Patent: Nov. 18, 2003

(54) RNASE P POLYPEPTIDES, POLYNUCLEOTIDES, AND METHODS USING THEIR MECHANISMS OF ACTION

(75) Inventors: Michael J. Gress, Wayne, PA (US); Lisa A Hegg, Devon, PA (US); Hu Li, Eagleville, PA (US); Joseph J. Park, King of Prussia, PA (US)

(73) Assignees: SmithKline Beecham Corporation, Philadelphia, PA (US); SmithKline Beecham P.L.C., Brentford Middlesex (GB)

(*) Notice: Subject to any disclaimer, the term of this patent is extended or adjusted under 35 U.S.C. 154(b) by 0 days.

(21) Appl. No.: 10/009,457
(22) PCT Filed: May 4, 2000
(86) PCT No.: PCT/US00/12252
§ 371 (c)(1),
(2), (4) Date: Nov. 5, 2001
(87) PCT Pub. No.: WO00/68430
PCT Pub. Date: Nov. 16, 2000

Related U.S. Application Data
(60) Provisional application No. 60/133,069, filed on May 7, 1999.

(51) Int. Cl.[7] .................. C07K 16/00; A61K 39/38
(52) U.S. Cl. .................. 530/388.4; 424/184.1
(58) Field of Search ............. 530/388.4; 424/184.1

(56) References Cited

FOREIGN PATENT DOCUMENTS

JP  10113189  5/1998

*Primary Examiner*—Hankyel T. Park
(74) *Attorney, Agent, or Firm*—Jason C. Fedon; Edward R. Gimmi; Charles Kinzig

(57) ABSTRACT

This invention relates to a novel bacterial ribonucleoprotein complex and the component parts thereof. More specifically, this invention relates to RNase P RNA isolated from *Staphylococcus aureus* and the use of RNase P RNA in screens for the identification of antimicrobial compounds and to the use of such compounds in therapy.

2 Claims, 1 Drawing Sheet

*Staphylococcus aureus* RnaseP RNA

Figure 1 *Staphylococcus aureus* RnaseP RNA
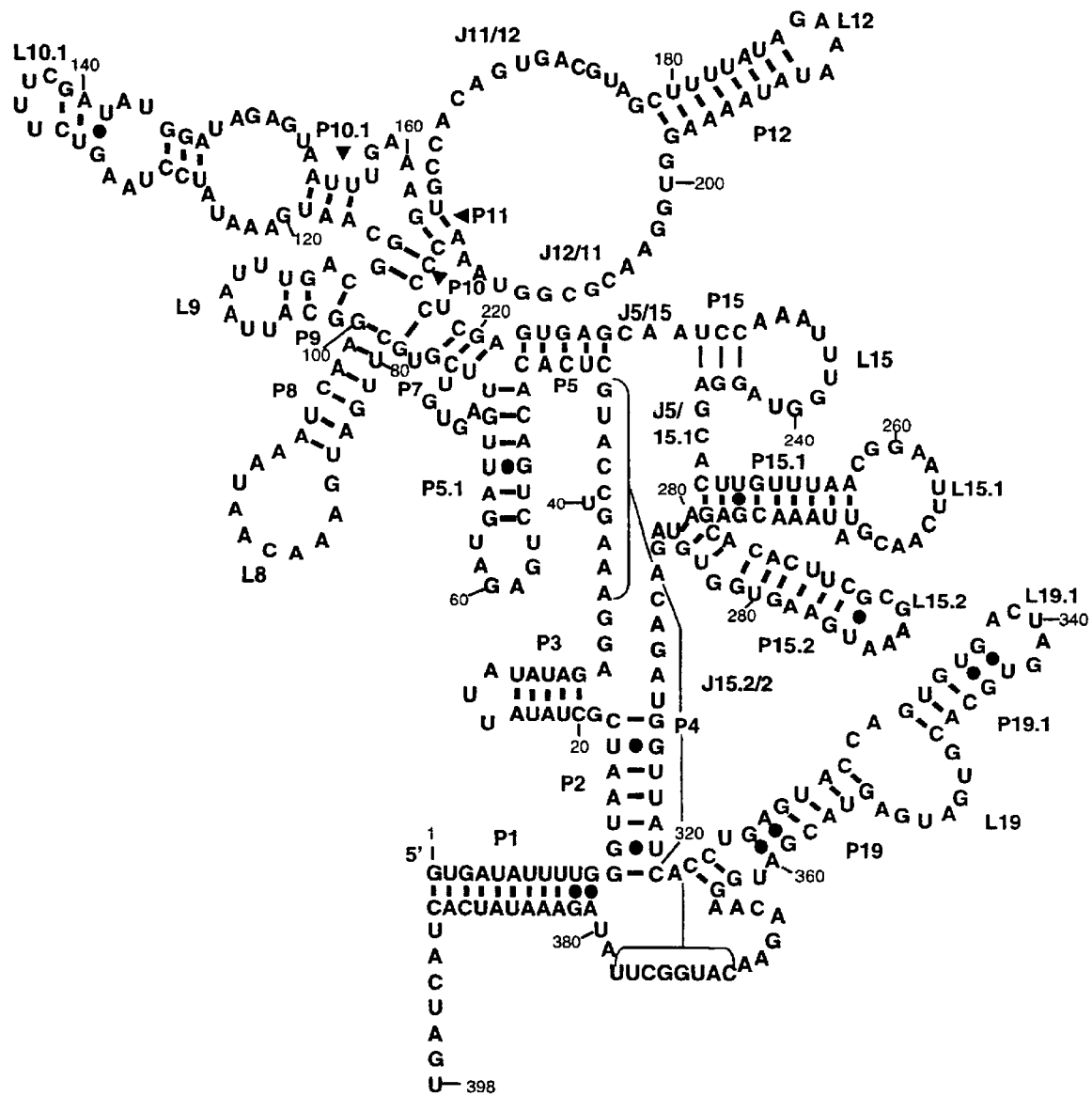

SEQUENCE LISTING

<160> NUMBER OF SEQ ID NOS: 14

<210> SEQ ID NO 1
<211> LENGTH: 354
<212> TYPE: DNA
<213> ORGANISM: Staphylococcus aureus

<400> SEQUENCE: 1

```
atgttattgg aaaaagctta ccgaattaaa aagaatgcag attttcagag aatatataaa      60
aaaggtcatt ctgtagccaa cagacaattt gttgtataca cttgtaataa taaagaaata     120
gaccattttc gcttaggtat tagtgtttct aaaaaactag gtaatgcagt gttaagaaac     180
aagattaaaa gagcaatacg tgaaaatttc aaagtacata agtcgcatat attggccaaa     240
gatattattg taatagcaag acagccagct aaagatatga cgactttaca aatacagaat     300
agtcttgagc acgtacttaa aattgccaaa gtttttaata aaaagattaa gtaa           354
```

<210> SEQ ID NO 2
<211> LENGTH: 117
<212> TYPE: PRT
<213> ORGANISM: Staphylococcus aureus

<400> SEQUENCE: 2

```
Met Leu Leu Glu Lys Val Tyr Arg Ile Lys Lys Asn Ala Asp Phe Gly
1               5                   10                  15

Arg Ile Tyr Lys Lys Gly His Ser Val Ala Asn Arg Gln Phe Val Val
            20                  25                  30

Tyr Thr Cys Asn Asn Lys Glu Ile Asp His Phe Arg Leu Gly Ile Ser
        35                  40                  45

Val Ser Lys Lys Leu Gly Asn Ala Val Leu Arg Asn Lys Ile Lys Arg
    50                  55                  60

Ala Ile Arg Glu Asn Phe Lys Val His Lys Ser His Ile Leu Ala Lys
65                  70                  75                  80
```

```
       Asp Ile Ile Val Ile Ala Arg Gln Pro Ala Lys Asp Met Thr Thr Leu
                    85                  90                  95

Gln Ile Gln Asn Ser Leu Glu His Val Leu Lys Ile Ala Lys Val Phe
               100                 105                 110

Asn Lys Lys Ile Lys
               115

<210> SEQ ID NO 3
<211> LENGTH: 400
<212> TYPE: DNA
<213> ORGANISM: Staphylococcus aureus

<400> SEQUENCE: 3
gttctgatat tttgggtaat cgctatatta tatagaggaa agtccatgct cacacagtct       60
gagatgattg tagtgttcgt gcttgatgaa acaataaatc aaggcattaa tttgacggca      120
atgaaatatc ctaagtcttt cgatatggat agagtaattt gaaagtgcca cagtgacgta      180
gcttttatag aaatataaaa ggtggaacgc ggtaaacccc tcgagtgagc aatccaaatt      240
tggtaggagc acttgtttaa cggaattcaa cgtataaacg agacacactt cgcgaaatga      300
agtggtgtac gacagatggt tatcacctga gtaccagtgt gactagtgca cgtgatgagt      360
acgatggaac agaacatggc ttatagaaat atcactacta                            400

<210> SEQ ID NO 4
<211> LENGTH: 64
<212> TYPE: DNA
<213> ORGANISM: Staphylococcus aureus
<220> FEATURE:
<221> NAME/KEY: unsure
<222> LOCATION: (30)(35)(39)(40)
<223> OTHER INFORMATION: Wherein n can be represented by a, c, t, or g

<400> SEQUENCE: 4
agactgaccc tagggttaag acttggcccn agggntatnn taacttactt taaaatgttt       60
tcac                                                                    64

<210> SEQ ID NO 5
<211> LENGTH: 24
<212> TYPE: DNA
<213> ORGANISM: Staphylococcus aureus

<400> SEQUENCE: 5
cgcgaagtgt gtctcgttta tacg                                              24

<210> SEQ ID NO 6
<211> LENGTH: 17
<212> TYPE: DNA
<213> ORGANISM: Staphylococcus aureus

<400> SEQUENCE: 6
gaggaaagtc catgctc                                                      17

<210> SEQ ID NO 7
<211> LENGTH: 24
<212> TYPE: DNA
<213> ORGANISM: Staphylococcus aureus

<400> SEQUENCE: 7
tttgttctaa ttttctcgtt atgc                                              24
```

<210> SEQ ID NO 8
<211> LENGTH: 87
<212> TYPE: DNA
<213> ORGANISM: Staphylococcus aureus

<400> SEQUENCE: 8
ccatagggta gggaatgaaa acattaaccc ctcaacgcat cccgaagtct tacctcagac    60
aaacgtttat cccatccctt acttttg                                       87

<210> SEQ ID NO 9
<211> LENGTH: 213
<212> TYPE: DNA
<213> ORGANISM: Staphylococcus aureus

<400> SEQUENCE: 9
gttttcattc cctaccctat ccttacttaa tcttttatt aaaaagaatg cagattttca    60
gagaatatat aaaaaaggtc attctgtagc caacagacaa tttgttgtat acacttgtaa   120
taataaagaa atagaccatt ttcgcttagg tattagtgtt tctaaaaaac taggtaatgc   180
agtgttaaga acaagattaa aagagcaata cgt                                213

<210> SEQ ID NO 10
<211> LENGTH: 215
<212> TYPE: DNA
<213> ORGANISM: Staphylococcus aureus

<400> SEQUENCE: 10
acgataaata acagtatgtt attggaaaaa gtctaccgaa ttaaaagaa tgcagatttt    60 cagagaatat ataaaaaagg tcattctgta gccaacagac aatttgttgt atacacttgt   120
aataataaag aaatagacca ttttcgctta ggtattagtg tttctaaaaa actaggtaat   180
gcagtgttaa gaacaagatt aaaagagcaa tacgt                              215

<210> SEQ ID NO 11
<211> LENGTH: 169
<212> TYPE: DNA
<213> ORGANISM: Staphylococcus aureus

<400> SEQUENCE: 11
gaaaatttca agtacataa gtcgcatata ttggccaaag attgtaatag caagacagcc    60
agctaaagat atgacgactt tacaaataca gaatagtctt gagcacgtac ttaaaattgc   120
caaagttttt aataaaaaga ttaagtaagg atagggtagg gaatgaaaa                169

<210> SEQ ID NO 12
<211> LENGTH: 93
<212> TYPE: RNA
<213> ORGANISM: Staphylococcus aureus

<400> SEQUENCE: 12
gggcgaauuc gccucggcua cguagcucag uugguuagag cacaucacuc auaaugaugg    60
ggucacaggu ucgaaucccg ucguagccac cag                                 93

<210> SEQ ID NO 13
<211> LENGTH: 17
<212> TYPE: DNA
<213> ORGANISM: Staphylococcus aureus

<400> SEQUENCE: 13
tgatatttct ggtaacc                                                   17

-continued

```
<210> SEQ ID NO 14
<211> LENGTH: 20
<212> TYPE: RNA
<213> ORGANISM: Staphylococcus aureus

<400> SEQUENCE: 14
guucugauau uuuggguaau                                               20
```

RNASE P POLYPEPTIDES, POLYNUCLEOTIDES, AND METHODS USING THEIR MECHANISMS OF ACTION

This is a 371 of International Application PCT/US00/12252, filed May 4, 2000, which claims benefit from the following Provisional Application: 60/133,069, filed May 7, 1999.

FIELD OF THE INVENTION

This invention relates to newly identified polynucleotides, polypeptides encoded by certain of these polynucleotides, molecular complexes of RNAs and polypeptides, the uses of such polynucleotides and polypeptides, as well as the production of such polynucleotides and polypeptides and recombinant host cells transformed with the polynucleotides. The invention relates particularly to such polynucleotides and polypeptides from Staphylococci, especially *S. aureus*. This invention also relates to inhibiting the biosynthesis, assembly or action of such polynucleotides and/or polypeptides and to the use of such inhibitors in therapy.

BACKGROUND OF THE INVENTION

This invention relates to a novel bacterial ribonucleoprotein complex and the component parts thereof. More specifically, this invention relates to RNase P, particularly RNase P from *Staphylococcus aureus*, and the use of RNase P or components thereof in screens for the identification of antimicrobial compounds and to the use of such compounds in therapy.

The Staphylococci make up a medically important genera of microbes. They are known to produce two types of disease, invasive and toxigenic. Invasive infections are characterized generally by abscess formation effecting both skin surfaces and deep tissues. *S. aureus* is the second leading cause of bacteremia in cancer patients. Osteomyelitis, septic arthritis, septic thrombophlebitis and acute bacterial endocarditis are also relatively common. There are at least three clinical conditions resulting from the toxigenic properties of Staphylococci. The manifestation of these diseases result from the actions of exotoxins as opposed to tissue invasion and bacteremia. These conditions include: Staphylococcal food poisoning, scalded skin syndrome and toxic shock syndrome.

The frequency of *Staphylococcus aureus* infections has risen dramatically in the past 20 years. This has been attributed to the emergence of multiply antibiotic resistant strains and an increasing population of people with weakened immune systems. It is no longer uncommon to isolate *Staphylococcus aureus* strains which are resistant to some or all of the standard antibiotics. This has created a demand for both new anti-microbial agents and diagnostic tests for this organism.

While certain Staphylococcal proteins associated with pathogenicity have been identified, e.g., coagulase, hemolysins, leucocidins and exo- and enterotoxins, additional targets are always useful because it is appreciated that the target of a antimicrobial screen can often bias the outcome. Thus, new targets allow for the discovery of new classes of antimicrobials.

BRIEF DESCRIPTION OF THE INVENTION

In accordance with another aspect of the invention, there is provided the use of a polynucleotide of the invention for therapeutic or prophylactic purposes, in particular genetic immunization. Among the particularly preferred embodiments of the invention are naturally occurring allelic variants of RNaseP and polypeptides encoded thereby.

In accordance with yet another aspect of the invention, there are provided inhibitors to such polypeptides, useful as antibacterial agents, including, for example, antibodies.

In accordance with certain preferred embodiments of the invention, there are provided products, compositions and methods for assessing RNaseP expression, treating disease, for example, disease, such as, infections of the upper respiratory tract (e.g., otitis media, bacterial tracheitis, acute epiglottitis, thyroiditis), lower respiratory (e.g., empyema, lung abscess), cardiac (e.g., infective endocarditis), gastrointestinal (e.g., secretory diarrhoea, splenic abscess, retroperitoneal abscess), CNS (e.g., cerebral abscess), eye (e.g., blepharitis, conjunctivitis, keratitis, endophthalmitis, preseptal and orbital cellulitis, darcryocystitis), kidney and urinary tract (e.g., epididymitis, intrarenal and perinephric absces, toxic shock syndrome), skin (e.g., impetigo, folliculitis, cutaneous abscesses, cellulitis, wound infection, bacterial myositis) bone and joint (e.g., septic arthritis, osteomyelitis), assaying genetic variation, and administering a RNaseP polypeptide or polynucleotide to an organism to raise an immunological response against a bacteria, especially a *Staphylococcus aureus* bacteria.

In certain preferred embodiments of the invention there are provided antibodies against RNaseP polypeptides.

In other embodiments of the invention there are provided methods for identifying compounds which bind to or otherwise interact with and inhibit or activate an activity of a polypeptide or polynucleotide of the invention comprising: contacting a polypeptide or polynucleotide of the invention with a compound to be screened under conditions to permit binding to or other interaction between the compound and the polypeptide or polynucleotide to assess the binding to or other interaction with the compound, such binding or interaction being associated with a second component capable of providing a detectable signal in response to the binding or interaction of the polypeptide or polynucleotide with the compound; and determining whether the compound binds to or otherwise interacts with and activates or inhibits an activity of the polypeptide or polynucleotide by detecting the presence or absence of a signal generated from the binding or interaction of the compound with the polypeptide or polynucleotide.

In accordance with yet another aspect of the invention, there are provided RNaseP agonists and antagonists, preferably bacteriostatic or bacteriocidal agonists and antagonists.

A preferred embodiment of the invention provides an antagonist that inhibits or an agonist that activates an activity of an RNA selected from the group consisting of: an RNA transcribed from a polynucleotide comprising an nucleotide sequence having at least a 90% identity to the amino acid sequence of SEQ ID NO:3, and an RNA transcribed from a polynucleotide comprising an nucleotide sequence set forth in SEQ ID NO:3, wherein said activity is selected from the group consisting of: *Staphylococcus aureus* RNaseP $K_m=53\pm4$ nM determined in a reaction in 1×buffer comprising 100 mM Tris-Cl, pH7.0, 150 mM KCl, 10 mM MgCl2, 5% PEG, and [E]=20 nM using cloned pre-tRNA$^{phe}$ as a substrate;

*Staphylococcus aureus* RNaseP $k_{cat}=3.4\pm0.1$ min$^{-1}$ determined in a reaction in 1×buffer comprising 100 mM Tris-Cl, pH7.0, 150 mM KCl, 10 mM MgCl2, 5% PEG, and [E]=20 nM using cloned pre-tRNA$^{phe}$ as a substrate; *Staphylococcus aureus* RNaseP RNA binding isotherm of $K_j$=8=1 nM for RNaseP protein determined in a reaction buffer comprising 20 mM K-Hepes, pH8.0, 0.01% NP-40, 400 mM NH$_4$OAc, 10 mM MgCl$_2$, and 5% glycererol; *Staphylococcus aureus* RNaseP V1 cleavage of nucleotides selected from the group consisting of: 8–11, 16–23, 30–33, 37–54, 64–84, 96–105, 119–130, 150–156, 166–169, 181–184, and 290–294; and *Staphylococcus aureus* RNase T2 cleavage of nucleotides selected from the group consisting of: 24–27, 55–60, 86–91, 106–108, 135–138, and 170–177; and said compound modulates the DEPC cleavage of nucleotides selected from the group consisting of: 159–161, A211–213.A203, 204, and A169, 292–294 (L15.2), 271 (bulged A).

Further provided is a method for the treatment of an individual having need to inhibit or activate RNAseP RNA or holoenzyme comprising the steps of: administering to the individual an antibacterially effective amount of an antagonist that inhibits or an agonist that activates an activity of a RNA selected from the group consisting of: an RNA transcribed from a polynucleotide comprising an nucleotide sequence having at least a 90% identity to the amino acid sequence of SEQ ID NO:3, and an RNA transcribed from a polynucleotide comprising an nucleotide sequence set forth in SEQ ID NO:3, wherein said activity is selected from the group consisting of: *Staphylococcus aureus* RNaseP $K_m$=53±4 nM determined in a reaction in 1×buffer comprising 100 mM Tris-Cl, pH7.0, 150 mM KCl, 10 mM MgCl2, 5% PEG, and [E]=20 nM using cloned pre-tRNA$^{phe}$ as a substrate; *Staphylococcus aureus* RNaseP $k_{cat}$=3.4±0.1 min$^{-1}$ determined in a reaction in 1×buffer comprising 100 mM Tris-Cl, pH7.0, 150 mM KCl, 10 mM MgCl2, 5% PEG, and [E]=20 nM using cloned pre-tRNA$^{phe}$ as a substrate; *Staphylococcus aureus* RNaseP RNA binding isotherm of $K_d$=8±1 nM for RNaseP protein determined in a reaction buffer comprising 20 MM K-Hepes, pH8.0, 0.01% NP-40, 400 mM NH$_4$OAc, 10 mM MgCl$_2$, and 5% glycererol; *Staphylococcus aureus* RNaseP V1 cleavage of nucleotides selected from the group consisting of: 8–11, 16–23, 30–33, 37–54, 64–84, 96–105, 119–130, 150–156, 166–169, 181–184, and 290–294; and *Staphylococcus aureus* RNase T2 cleavage of nucleotides selected from the group consisting of: 24–27, 55–60, 86–91, 106–108, 135–138, and 170–177; and said compound modulates the DEPC cleavage of nucleotides selected from the group consisting of: 159–161, A211 –213.A203, 204, and A169, 292–294 (L15.2), 271(bulged A).

Still further provided is a method for the treatment of an individual infected with a bacteria comprising the steps of administering to the individual an antibacterially effective amount of an antagonist that inhibits or an agonist that activates an activity of a RNA selected from the group consisting of: an RNA transcribed from a polynucleotide comprising an nucleotide sequence having at least a 90% identity to the amino acid sequence of SEQ ID NO:3, and an RNA transcribed from a polynucleotide comprising an nucleotide sequence set forth in SEQ ID NO:3, wherein said activity is selected from the group consisting of: *Staphylococcus aureus* RNaseP $K_m$=53±4 nM determined in a reaction in 1×buffer comprising 100 mM Tris-Cl, pH7.0, 150 mM KCl, 10 mM MgCl2, 5% PEG, and [E]=20 nM using cloned pre-tRNA$^{phe}$ as a substrate; *Staphylococcus aureus* RNaseP $k_{cat}$=3.4±0.1 min$^{-1}$ determined in a reaction in 1×buffer comprising 100 mM Tris-Cl, pH7.0, 150 mM KCl, 10 mM MgCl2, 5% PEG, and [E]=20 nM using cloned pre-tRNA$^{phe}$ as a substrate; *Staphylococcus aureus* RNaseP RNA binding isotherm of $K_d$=8±1 nM for RNaseP protein determined in a reaction buffer comprising 20 mM K-Hepes, pH8.0, 0.01% NP-40, 400 mM NH$_4$OAc, 10 mM MgCl$_2$, and 5% glycererol; *Staphylococcus aureus* RNaseP V1 cleavage of nucleotides selected from the group consisting of: 8–11, 16–23, 30–33, 37–54, 64–84, 96–105, 119–130, 150–156, 166–169, 181–184, and 290–294; and *Staphylococcus aureus* RNase T2 cleavage of nucleotides selected from the group consisting of: 24–27, 55–60, 86–91, 106–108, 135–138, and 170–177; and said compound modulates the DEPC cleavage of nucleotides selected from the group consisting of: 159–161, A211–213.A203, 204, and A169, 292–294 (L15.2), 271(bulged A).

Preferred methods are also provided wherein said bacteria is selected from the group consisting of: a member of the genus Staphylococcus, *Staphylococcus aureus*, a member of the genus Streptococcus, and *Streptococcus pneumoniae*.

Another preferred embodiment of the invention is a method for the treatment of an individual having need to inhibit or activate RNaseP RNA or holoenzyme comprising the steps of administering to the individual an antibacterially effective amount of an antagonist that inhibits or an agoinist that activates an activity of RNaseP RNA or holoenzyme selected from the group consisting of: *Staphylococcus aureus* RNaseP $K_m$=53±4 nM determined in a reaction in 1×buffer comprising 100 mM Tris-Cl, pH7.0, 150 mM KCl, 10 mM MgCl2, 5% PEG, and [E]=20 nM using cloned pre-tRNA$^{phe}$ as a substrate; *Staphylococcus aureus* RNaseP $k_{cat}$=3.4±0.1 min$^{-1}$ determined in a reaction in 1×buffer comprising 100 mM Tris-Cl, pH7.0, 150 mM KCl, 10 mM MgCl2, 5% PEG, and [E]=20 nM using cloned pre-tRNA$^{phe}$ as a substrate; *Staphylococcus aureus* RNaseP RNA binding isotherm of $K_d$=8±1 nM for RNaseP protein determined in a reaction buffer comprising 20 mM K-Hepes, pH8.0, 0.01% NP-40, 400 mM NH$_4$OAc, 10 mM MgCl$_2$, and 5% glycererol; *Staphylococcus aureus* RNaseP V1 cleavage of nucleotides selected from the group consisting of: 8–11, 16–23, 30–33, 37–54, 64–84, 96–105, 119–130, 150–156, 166–169, 181–184, and 290–294; and *Staphylococcus aureus* RNase T2 cleavage of nucleotides selected from the group consisting of: 24–27, 55–60, 86–91, 106–108, 135–138, and 170–177; and said compound modulates the DEPC cleavage of nucleotides selected from the group consisting of: 159–161, A211–213.A203, 204, and A169, 292–294 (L15.2), 271(bulged A).

A further provided embodiment of the invention provides a method for the treatment of an individual infected with a bacteria comprising the steps of administering to the individual an antibacterially effective amount of an antagonist that inhibits or an agonist that activates that activates an activity of RNaseP selected from the group consisting of: *Staphylococcus aureus* RNaseP $K_m$=53±4 nM determined in a reaction in 1×buffer comprising 100 mM Tris-Cl, pH7.0, 150 mM KCl, 10 mM MgCl2, 5% PEG, and [E]=20 nM using cloned pre-tRNA$^{phe}$ as a substrate; *Staphylococcus aureus* RNaseP $k_{cat}$=3.4±0.1 min$^{-1}$ determined in a reaction in 1×buffer comprising 100 mM Tris-Cl, pH7.0, 150 mM KCl, 10 mM MgCl2, 5% PEG, and [E]=20 nM using cloned pre-tRNA$^{phe}$ as a substrate; *Staphylococcus aureus* RNaseP RNA binding isotherm of $K_d$=8±1 nM for RNaseP protein determined in a reaction buffer comprising 20 mM K-Hepes, pH8.0, 0.01% NP-40, 400 mM NH$_4$OAc, 10 mM MgCl$_2$, and 5% glycererol; *Staphylococcus aureus* RNaseP V1 cleavage of nucleotides selected from the group consisting of: 8–11, 16–23, 30–33, 37–54, 64–84, 96–105, 119–130, 150–156, 166–169, 181–184, and 290–294; and *Staphylococcus aureus* RNase T2 cleavage of nucleotides selected from the group consisting of: 24–27, 55–60, 86–91, 106–108, 135–138, and 170–177; and said compound modulates the DEPC cleavage of nucleotides selected from the group consisting of: 159–161, A211–213.A203, 204, and A 169, 292–294 (L15.2), 271(bulged A).

A further method for the treatment of an individual infected by *Streptococcus pneumoniae* is provided comprising the steps of administering to the individual an antibacterially effective amount of an antagonist that inhibits or anagonist that activates an activity of *Streptococcus pneumoniae* RNAseP RNA or holoenzyme selected from the group consisting of: *Staphylococcus aureus* RNaseP $K_m$=53±4 nM determined in a reaction in 1×buffer comprising 100 mM Tris-Cl, pH7.0, 150 mM KCl, 10 mM MgCl2, 5% PEG, and [E]=20 nM using cloned pre-tRNA$^{phe}$ as a substrate; *Staphylococcus aureus* RNaseP $k_{cat}$=3.4±0.1 min$^{-1}$ determined in a reaction in 1×buffer comprising 100 mM Tris-Cl, pH7.0, 150 mM KCl, 10 mM MgCl2, 5% PEG, and [E]=20 nM using cloned pre-tRNA$^{phe}$ as a substrate; *Staphylococcus aureus* RNaseP RNA binding isotherm of $K_d$=8±1 nM for RNaseP protein determined in a reaction buffer comprising 20 mM K-Hepes, pH8.0, 0.01% NP-40, 400 mM NH$_4$OAc, 10 mM MgCl$_2$, and 5% glycererol; *Staphylococcus aureus* RNaseP V1 cleavage of nucleotides selected from the group consisting of: 8–11, 16–23, 30–33, 37–54, 64–84, 96–105, 119–130, 150–156, 166–169, 181–184, and 290–294; and *Staphylococcus aureus* RNase T2 cleavage of nucleotides selected from the group consisting of: 24–27, 55–60, 86–91, 106–108, 135–138, and 170–177; and said compound modulates the DEPC cleavage of nucleotides selected from the group consisting of: 159–161, A211–213.A203, 204, and A169, 292–294 (L15.2), 271(bulged A).

Still further provided is an antagonist that inhibits an activity of a polypeptide selected from the group consisting of: an RNA transcribed from a polynucleotide comprising an nucleotide sequence having at least a 90% identity to the amino acid sequence of SEQ ID NO:3, and an RNA transcribed from a polynucleotide comprising an nucleotide sequence set forth in SEQ ID NO:3, wherein said activity is selected from the group consisting of: *Staphylococcus aureus* RNaseP $K_m$=53±4 nM determined in a reaction in 1×buffer comprising 100 mM Tris-Cl, pH7.0, 150 mM KCl, 10 mM MgCl2, 5% PEG, and [E]=20 nM using cloned pre-tRNA$^{phe}$ as a substrate; *Staphylococcus aureus* RNaseP $k_{cat}$=3.4±0.1 min$^{-1}$ determined in a reaction in 1×buffer comprising 100 mM Tris-Cl, pH7.0, 150 mM KCl, 10 mM MgCl2, 5% PEG, and [E]=20 nM using cloned pre-tRNA$^{phe}$ as a substrate; *Staphylococcus aureus* RNaseP RNA binding isotherm of $K_d$=8±1 nM for RNaseP protein determined in a reaction buffer comprising 20 mM K-Hepes, pH8.0, 0.01% NP-40, 400 mM NH$_4$OAc, 10 mM MgCl$_2$, and 5% glycererol; *Staphylococcus aureus* RNaseP V1 cleavage of nucleotides selected from the group consisting of: 8–11, 16–23, 30–33, 37–54, 64–84, 96–105, 119–130, 150–156, 166–169, 181–184, and 290–294; and *Staphylococcus aureus* RNase T2 cleavage of nucleotides selected from the group consisting of: 24–27, 55–60, 86–91, 106–108, 135–138, and 170–177; and said compound modulates the DEPC cleavage of nucleotides selected from the group consisting of: 159–161, A211–213.A203, 204, and A169, 292–294 (L15.2), 271(bulged A).

Also provided is a method for the treatment of an individual having need to inhibit RNaseP RNA or holoenzyme comprising the steps of administering to the individual an antibacterially effective amount of an antagonist that inhibits an activity of a polypeptide selected from the group consisting of: an RNA transcribed from a polynucleotide comprising an nucleotide sequence having at least a 90% identity to the amino acid sequence of SEQ ID NO:3, and an RNA transcribed from a polynucleotide comprising an nucleotide sequence set forth in SEQ ID NO:3; *Staphylococcus aureus* RNaseP $K_m$=53±4 nM determined in a reaction in 1×buffer comprising 100 mM Tris-Cl, pH7.0, 150 mM KCl, 10 mM MgCl2, 5% PEG, and [E]=20 nM using cloned pre-tRNA$^{phe}$ as a substrate; *Staphylococcus aureus* RNaseP $k_{cat}$=3.4±0.1 min$^{-1}$ determined in a reaction in 1×buffer comprising 100 mM Tris-Cl, pH7.0, 150 mM KCl, 10 mM MgCl2, 5% PEG, and [E]=20 nM using cloned pre-tRNA$^{phe}$ as a substrate; *Staphylococcus aureus* RNaseP RNA binding isotherm of $K_d$=8±1 nM for RNaseP protein determined in a reaction buffer comprising 20 mM K-Hepes, pH8.0, 0.01% NP-40, 400 mM NH$_4$OAc, 10 mM MgCl$_2$, and 5% glycererol; *Staphylococcus aureus* RNaseP V1 cleavage of nucleotides selected from the group consisting of: 8–11, 16–23, 30–33, 37–54, 64–84, 96–105, 119–130, 150–156, 166–169, 181–184, and 290–294; and *Staphylococcus aureus* RNase T2 cleavage of nucleotides selected from the group consisting of: 24–27, 55–60, 86–91, 106–108, 135–138, and 170–177; and said compound modulates the DEPC cleavage of nucleotides selected from the group consisting of: 159–161, A211–213.A203, 204, and A169, 292–294 (L15.2), 271(bulged A).

Another preferred embodiment of the invention provides a method for inhibiting an activity of RNAseP RNA or holoenzyme comprising the steps of contacting a composition comprising said polypeptide with an effective amount of an antagonist that inhibits an activity of RNaseP, wherein said activity is selected from the group consisting of: *Staphylococcus aureus* RNaseP $K_m$=53±4 nM determined in a reaction in 1×buffer comprising 100 mM Tris-Cl, pH7.0, 150 mM KCl, 10 mM MgCl2, 5% PEG, and [E]=20 nM using cloned pre-tRNA$^{phe}$ as a substrate; *Staphylococcus aureus* RNaseP $k_{cat}$=3.4±0.1 min$^{-1}$ determined in a reaction in 1×buffer comprising 100 mM Tris-Cl, pH7.0, 150 mM KCl, 10 mM MgCl2, 5% PEG, and [E]=20 nM using cloned pre-tRNA$^{phe}$ as a substrate; *Staphylococcus aureus* RNaseP RNA binding isotherm of $K_d$=8±1 nM for RNaseP protein determined in a reaction buffer comprising 20 mM K-Hepes, pH8.0, 0.01% NP-40, 400 mM NH$_4$OAc. 10 mM MgCl$_2$, and 5% glycererol; *Staphylococcus aureus* RNaseP V1 cleavage of nucleotides selected from the group consisting of: 8–11, 16–23, 30–33, 37–54, 64–84, 96–105, 119–130, 150–156, 166–169, 181–184, and 290–294; and *Staphylococcus aureus* RNase T2 cleavage of nucleotides selected from the group consisting of: 24–27, 55–60, 86–91, 106–108, 135–138, and 170–177; and said compound modulates the DEPC cleavage of nucleotides selected from the group consisting of: 159–161, A211 –213.A203, 204, and A169, 292–294 (L15.2), 271(bulged A).

The invention provides a method for inhibiting an activity of RnaseP RNA or holoenzyme, wherein said activity is selected from the group consisting of: *Staphylococcus aureus* RNaseP KM=53±4 nM determined in a reaction in 1×buffer comprising 100 mM Tris-Cl, pH7.0, 150 mM KCl, 10 mM MgCl2, 5% PEG, and [E]=20 nM using cloned pre-tRNA$^{phe}$ as a substrate; *Staphylococcus aureus* RNaseP $k_{cat}$=3.4±0.1 min$^{-1}$ determined in a reaction in 1×buffer comprising 100 mM Tris-Cl, pH7.0, 150 mM KCl, 10 mM MgCl2, 5% PEG, and [E]=20 nM using cloned pre-tRNA$^{phe}$ as a substrate; *Staphylococcus aureus* RNaseP RNA binding isotherm of $K_d$=8±1 nM for RNaseP protein determined in a reaction buffer comprising 20 mM K-Hepes, pH8.0, 0.01% NP-40, 400 mM NH$_4$OAc, 10 mM MgCl$_2$, and 5% glycererol; *Staphylococcus aureus* RNaseP V1 cleavage of nucleotides selected from the group consisting of: 8–11, 16–23, 30–33, 37–54, 64–84, 96–105, 119–130, 150–156, 166–169, 181–184, and 290–294; and *Staphylococcus aureus* RNase T2 cleavage of nucleotides selected from the group consisting of: 24–27, 55–60, 86–91, 106–108, 135–138, and 170–177; and said compound modulates the DEPC cleavage of nucleotides selected from the group consisting of: 159–161, A211–213.A203, 204, and A169, 292–294 (L15.2), 271(bulged A).

Also provided is a method for inhibiting a growth of bacteria comprising the steps of contacting a composition comprising bacteria with an antibacterially effective amount of an antagonist that inhibits an activity of RNAseP RNA or holoenzyme, wherein said activity is selected from the group consisting of: *Staphylococcus aureus* RNaseP $K_m$=53±4 nM determined in a reaction in 1×buffer comprising 100 mM Tris-Cl, pH7.0, 150 mM KCl, 10 mM MgCl2, 5% PEG, and [E]=20 nM using cloned pre-tRNA$^{phe}$ as a substrate; *Staphylococcus aureus* RNaseP $k_{cat}$=3.4±0.1 min$^{-1}$ determined in a reaction in 1×buffer comprising 100 mM Tris-Cl, pH7.0, 150 mM KCl, 10 mM MgCl2, 5% PEG, and [E]=20 nM using cloned pre-tRNA$^{phe}$ as a substrate; *Staphylococcus aureus* RNaseP RNA binding isotherm of $K_d$=8±1 nM for RNaseP protein determined in a reaction buffer comprising 20 mM K-Hepes, pH8.0, 0.01% NP-40, 400 mM NH$_4$OAc, 10 mM MgCl$_2$, and 5% glycererol; *Staphylococcus aureus* RNaseP V1 cleavage of nucleotides selected from the group consisting of: 8–11, 16–23, 30–33, 37–54, 64–84, 96–105, 119–130, 150–156, 166–181–184, and 290–294; and *Staphylococcus aureus* RNase T2 cleavage of nucleotides selected from the group consisting of: 24–27, 55–60, 86–91, 106–108, 135–138, and 170–177; and said compound modulates the DEPC cleavage of nucleotides selected from the group consisting of: 159–161, A211–213.A203, 204, and A169, 292–294 (L15.2), 271(bulged A).

Another embodiment of the invention is a method for inhibiting a RNaseP RNA or holoenzyme comprising the steps of contacting a composition comprising bacteria with an antibacterially effective amount of an antagonist that inhibits an activity of RNaseP, wherein said activity is selected from the group consisting of: *Staphylococcus aureus* RNaseP $K_m$=53±4 nM determined in a reaction in 1×buffer comprising 100 mM Tris-Cl, pH7.0, 150 mM KCl, 10 mM MgCl2, 5% PEG, and [E]=20 nM using cloned pre-tRNA$^{phe}$ as a substrate; *Staphylococcus aureus* RNaseP $k_{cat}$=3.4±0.1 min$^{-1}$ determined in a reaction in 1×buffer comprising 100 mM Tris-Cl, pH7.0, 150 mM KCl, 10 mM MgCl2, 5% PEG, and [E]=20 nM using cloned pre-tRNA$^{phe}$ F as a substrate; *Staphylococcus aureus* RNaseP RNA binding isotherm of $K_d$=8±1 nM for RNaseP protein determined in a reaction buffer comprising 20 mM K-Hepes, pH8.0, 0.01% NP-40, 400 mM NH,OAc, 10 mM MgCl$_2$, and 5% glycererol; *Staphylococcus aureus* RNaseP V1 cleavage of nucleotides selected from the group consisting of: 8–11, 16–23, 30–33, 37–54, 64–84, 96–105, 119–130, 150–156, 166–169, 181–184, and 290–294; and *Staphylococcus aureus* RNase T2 cleavage of nucleotides selected from the group consisting of: 24–27, 55–60, 86–91, 106–108, 135–138, and 170–177; and said compound modulates the DEPC cleavage of nucleotides selected from the group consisting of: 159–161, A211–213.A203, 204, and A 169, 292–294 (L15.2), 271(bulged A).

In a further aspect of the invention there are provided compositions comprising a RNaseP polynucleotide or a RNaseP polypeptide for administration to a cell or to a multicellular organism.

Various changes and modifications within the spirit and scope of the disclosed invention will become readily apparent to those skilled in the art from reading the following descriptions and from reading the other parts of the present disclosure.

BRIEF DESCRIPTION OF THE DRAWINGS

FIG. 1 shows secondary and tertiary structures of *S. aureus* RNase P RNA modeled based on structural probing data and genetic comparison.

GLOSSARY

The following definitions are provided to facilitate understanding of certain terms used frequently herein. Certain other definitions are provided elsewhere herein.

"Host cell" is a cell which has been transformed or transfected, or is capable of transformation or transfection by an exogenous polynucleotide sequence.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math.*, 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., *Nucleic Acids Research* 12(1): 387 (1984)), BLASTP, BLASTN, and FASTA (Atschul, S. F. et al., *J. Molec. Biol.* 215: 403–410 (1990). The BLAST X program is publicly available from NCBI and other sources (*BLAST Manual*, Altschul, S., et al., NCBI NLM NIH Bethesda, Md. 20894; Altschul, S., et al., *J. Mol. Biol.* 215: 403–410 (1990). As an illustration, by a polynucleotide having a nucleotide sequence having at least, for example, 95% "identity" to a reference nucleotide sequence of SEQ ID NO: 1 it is intended that the nucleotide sequence of the polynucleotide is identical to the reference sequence except that the polynucleotide sequence may include up to five point mutations per each 100 nucleotides of the reference nucleotide sequence of SEQ ID NO:1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having an amino acid sequence having at least, for example, 95% identity to a reference amino acid sequence of SEQ ID NO:2 is intended that the amino acid sequence of the polypeptide is identical to the reference sequence except that the polypeptide sequence may include up to five amino acid alterations per each 100 amino acids of the reference amino acid of SEQ ID NO:2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein.

"Polynucleotide(s)" generally refers to any polyribonucleotide or polydeoxribonucleotide, which may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells. including, for example, simple and complex cells. "Polynucleotide(s)" also embraces short polynucleotides often referred to as oligonucleotide(s).

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, *PROTEINS—STRUCTURE AND MOLECULAR PROPERTIES*, 2nd Ed., T. E. Creighton, W. H. Freeman and Company, New York (1993) and Wold, F., Posttranslational Protein Modifications: Perspectives and Prospects, pgs. 1–12 in *POSTTRANSLATIONAL COVALENT MODIFICATION OF PROTEINS*, B. C. Johnson, Ed., Academic Press, New York (1983); Seifter et al., *Meth. Enzymol.* 182:626–646 (1990) and Rattan et al., *Protein Synthesis: Posttranslational Modifications and Aging*, Ann. N.Y. Acad. Sci. 663: 48–62 (1992). Polypeptides may be branched or cyclic, with or without branching. Cyclic, branched and branched circular polypeptides may result from post-translational natural processes and may be made by entirely synthetic methods, as well.

"Variant(s)" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

DETAILED DESCRIPTION OF THE INVENTION

The ribonucleoprotein, RNase P, plays a key role in the biosynthesis of transfer RNA (tRNA), itself a key intermediate in protein biosynthesis. RNase P functions to process precursor RNAs into mature tRNAs by endoribonucleolytic action. The complex in prokaryotes is composed of two subunits: a catalytic RNA and protein co-factor. Recent reviews of certain RNase P molecules exist. See for example, L. A. Kirsebom, *Molecular Microbiology* 17(3), 411–420 (1995) or N. R. Pace and J. W. Brown, *J. Bacteriol.* 177 (8), 1919–1928 (1995).

The invention relates to novel RNaseP polypeptides and polynucleotides as described in greater detail below. In particular, the invention relates to polypeptides and polynucleotides of a novel RNaseP of *Staphylococcus aureus*, which is related by amino acid sequence homology to RNase P polypeptide set forth in SEQ ID NO:2. The invention relates especially to RNaseP having the nucleotide and amino acid sequences set out in Table 1, SEQ ID NO: 1 and SEQ ID NO:2 respectively, and to the RNaseP nucleotide sequences of the DNA in the deposited strain and amino acid sequences encoded thereby. The invention also relates to the RNase P RNA component, particularly in its catalytic for, and sequences from which such component is transcribed.

RNase P RNA Component

Phylogenetic comparisons readily allow secondary structure modeling and the identification of a minimum consensus structure. Data concerning the RNase P RNA structure are available in the RNase P database on http://jwbrown.mbio.ncsu.edu/RNaseP/home.html. A polynucleotide of the invention from which the RNA component is transcribed is set forth in [SEQ ID NO:14].

In general, few nucleotides are conserved but compensatory base changes in hydrogen bonded regions show that the overall structure is preserved throughout eubacteria. Universal conservation of primary sequences (*E. coli*:61–74, 353–360) together with other conserved or quasi-conserved nucleotides implicate functional importance, the significance of which remain unknown. To date all RNase P RNA molecules can be folded to fit a consensus 'cage-like' structure, beyond this domain there is no convincing structural similarity between prokaryotic and eukaryotic RNase P RNAs.

RNase P Protein Component

The precise functional role of the protein remains unknown. While it is appreciated that in vitro the experimental conditions can be established such that the protein component is not necessary for catalytic activity, in vivo, the protein components appears to be required. A novel RNase P protein component from *S. aureus* has been identified and is characterized by the amino acid sequence given in [SEQ ID NO:2] in which the *S. aureus* (Sau) sequence is aligned with sequences from other microorganisms.

The full length sequence encoding the intact RNase P protein component can be obtained by probing a genomic library by for example in situ colony hybridization detailed in Maniatis et al. (era) using a probe(s) generated based on the sequences given in [SEQ ID NOS: 1 and 2].

TABLE 1

RNaseP Polynucleotide and Polypeptide Sequences (A) Sequences from Staphylococcus aureus RNaseP polynucleotide sequence [SEQ ID NO:1].
5'-ATG TTA TTG GAA AAA GCT TAC CGA ATT AAA AAG AAT GCA GAT

TTT CAG AGA ATA TAT AAA AAA GGT CAT TCT GTA GCC AAC AGA CAA

TTT GTT GTA TAC ACT TGT AAT AAT AAA GAA ATA GAC CAT TTT CGC

TTA GGT ATT AGT GTT TCT AAA AAA CTA GGT AAT GCA GTG TTA AGA

AAC AAG ATT AAA AGA GCA ATA CGT GAA AAT TTC AAA GTA CAT AAG

TCG CAT ATA TTG GCC AAA GAT ATT ATT GTA ATA3GCA AGA CAG CCA

GCT AAA GAT ATG ACQ ACT TTA CAA ATA CAG AAT AGT CTT GAG CAC

GTA CTT AAA ATT GCC AAA GTT TTT AAT AAA AAG ATT AAG TAA-3'

(B) RNaseP polypeptide sequence deduced from the polynucleotide sequence in this table [SEQ ID NO:2].
NH$_2$- MLLEK VYRIK KNADF GRIYK KGHSV ANRQF VVYTC NNKEI DHFRL

GISVS KKLGN AVLRN KIKRA IRENF KVHKS HILAK DIIVI ARQPA KDMTT

LQIQN SLEHV LKIAK VFNKK IK-COOH (C) Polynucleotide sequence embodiments [SEQ ID NO:1].
X-(R$_1$)$_n$-ATG TTA TTG GAA AAA GCT TAC CGA ATT AAA AAG AAT GCA

GAT TTT CAG AGA ATA TAT AAA AAA GGT CAT TCT GTA GCC AAC AGA

CAA TTT GTT GTA TAC ACT TGT AAT AAT AAA GAA ATA GAC CAT TTT

CGC TTA GGT ATT AGT GTT TCT AAA AAA CTA GGT AAT GCA GTG TTA

TABLE 1-continued

RNaseP Polynucleotide and Polypeptide Sequences

AGA AAC AAG ATT AAA AGA GCA ATA CGT GAA AAT TTC AAA GTA CAT

AAG TCG CAT ATA TTG GCC AAA GAT ATT ATT GTA ATA GCA AGA CAG

CCA GCT AAA GAT ATG ACG ACT TTA CAA ATA CAG AAT AGT CTT GAG

CAC GTA CTT AAA ATT GCC AAA GTT TTT AAT AAA AAG ATT AAG TAA-

$(R_2)_n$-Y (D) Polypeptide sequence embodiments [SEQ ID NO:2].
X-$(R_1)_n$-MLLEK VYRIK KNADF GRIYK KGHSV ANRQF VVYTC NNKEI DHFRL

GISVS KKLGN AVLRN KIKRA IRENF KVHKS HILAK DIIVI ARQPA KDMTT

LQIQN SLEHV LKIAK VFNKK IK-$(R_2)_n$-Y (E) Sequences from *Staphylococcus aureus* RNaseP RNA gene [SEQ ID NO:3].
5'-GTTCTGATATTTTGGGTAATCGCTATATTATATAGAGGAAAGTCCATGCTCACACAGTCTGAGATGATT

GTAGTGTTCGTGCTTGATGAAACAATAAATCAAGGCATTAATTTGACGGCAATGAAATATCCTAAGTCT

TTCGATATGGATAGAGTAATTTGAAAGTGCCACAGTGACGTAGCTTTTATAGAAATATAAAAGGTGGAA

CGCGGTAAACCCCTCGAGTGAGCAATCCAAATTTGGTAGGAGCACTTGTTTAACGGAATTCAACGTAT

AAACGAGACACACTTCGCGAAATGAAGTGGTGTACGACAGATGGTTATCACCTGAGTACCAGTGTGA

CTAGTGCACGTGATGAGTACGATGGAACAGAACATGGCTTATAGAAATATCACTACTA

G-3'

(F) Polynucleotide sequence embodiments [SEQ ID NO:3].
X-$(R_1)_n$-

GTTCTGATATTTTGGGTAATCGCTATATTATATAGAGGAAAGTCCATGCTCACACAGTCTGAGATGATT

GTAGTGTTCGTGCTTGATGAAACAATAAATCAAGGCATTAATTTGACGGCAATGAAATATCCTAAGTCT

TTCGATATGGATAGAGTAATTTGAAAGTGCCACAGTGACGTAGCTTTTATAGAAATATAAAAGGTGGAA

CGCGGTAAACCCCTCGAGTGAGCAATCCAAATTTGGTAGGAGCACTTGTTTAACGGAATTCAACGTAT

AAACGAGACACACTTCGCGAAATGAAGTGGTGTACGACAGATGGTTATCACCTGAGTACCAGTGTGA

CTAGTGCACGTGATGAGTACGATGGAACAGAACATGGCTTATAGAAATATCACTACTA

G-$(R_2)_n$-Y

Polypeptides of the Invention

The polypeptides of the invention include the polypeptide of Table 1 [SEQ ID NO:2] (in particular the mature polypeptide) as well as polypeptides and fragments, particularly those which have the biological activity of RNaseP, and also those which have at least 70% identity to the polypeptide of Table 1 [SEQ ID NO:2] or the relevant portion, preferably at least 80% identity to the polypeptide of Table 1 [SEQ ID NO:2), and more preferably at least 90% similarity (more preferably at least 90% identity) to the polypeptide of Table 1 [SEQ ID NO:2] and still more preferably at least 95% similarity (still more preferably at least 95% identity) to the polypeptide of Table 1 (SEQ ID NO:2] and also include portions of such polypeptides with such portion of the polypeptide generally containing at least 30 amino acids and more preferably at least 50 amino acids.

The invention also includes polypeptides of the formula set forth in Table 1 (D) [SEQ ID NO:2] wherein, at the amino terminus, X is hydrogen, and at the carboxyl terminus, Y is hydrogen or a metal, $R_1$ and $R_2$ is any amino acid residue, and n is an integer between 1 and 1000. Any stretch of amino acid residues denoted by either R group, where R is greater than 1, may be either a heteropolymer or a homopolymer, preferably a heteropolymer.

A fragment is a variant polypeptide having an amino acid sequence that entirely is the same as part but not all of the amino acid sequence of the aforementioned polypeptides. As with RNaseP polypeptides fragments may be "freestanding," or comprised within a larger polypeptide of which they form a part or region, most preferably as a single continuous region, a single larger polypeptide.

Preferred fragments include, for example, truncation polyreptrides having a portion of the amino acid sequence of Table 1 [SEQ ID NO:2], or of variants thereof, such as a continuous series of residues that includes the amino terminus, or a continuous series of residues that includes the carboxyl terminus. Degradation forms of the polypeptides of the invention in a host cell, particularly a *Staphylococcus aureus*, are also preferred. Further preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Also preferred are biologically active fragments which are those fragments that mediate activities of RNaseP, including those with a similar activity or an improved activity, or with a decreased undesirable activity. Also included are those fragments that are antigenic or immunogenic in an animal, especially in a human. Particularly preferred are fragments comprising receptors or domains of enzymes that confer a function essential for viability of Staphylococcus aureus or the ability to initiate, or maintain cause disease in an individual, particularly a human.

Variants that are fragments of the polypeptides of the invention may be employed for producing the corresponding full-length polypeptide by peptide synthesis; therefore, these variants may be employed as intermediates for producing the full-length polypeptides of the invention.

POLYNUCLEOTIDES OF THE INVENTION

Another aspect of the invention relates to isolated polynucleotides, including the full length gene, that encode the RNaseP polypeptide having a deduced amino acid sequence of Table 1 [SEQ ID NO:2] and polynucleotides closely related thereto and variants thereof.

Using the information provided herein, such as a polynucleotide sequence set out in SEQ ID NOS: 1, 3, and 4, a polynucleotide of the invention encoding RNaseP polypeptide or RNA (such as that transcribed from SEQ ID NO:3) may be obtained using standard cloning and screening methods, such as those for cloning and sequencing chromosomal DNA fragments from bacteria using Staphylococcus aureus WCUH 29 cells as starting material, followed by obtaining a full length clone. For example, to obtain a polynucleotide sequence of the invention, such as a sequence given in SEQ ID NOS:1, 3, and 4, typically a library of clones of chromosomal DNA of Staphylococcus aureus WCUH 29 in E. coli or some other suitable host is probed with a radiolabeled oligonucleotide, preferably a 7-mer or longer, derived from a partial sequence. Clones carrying DNA identical to that of the probe can then be distinguished using stringent conditions. By sequencing the individual clones thus identified with sequencing primers designed from the original sequence it is then possible to extend the sequence in both directions to determine the full gene sequence. Conveniently, such sequencing is performed using denatured double stranded DNA prepared from a plasmid clone. Suitable techniques are described by Maniatis, T., Fritsch, E. F. and Sambrook et al., MOLECULAR CLONING, A LABORATORY MANUAL, 2nd Ed.; Cold Spring Harbor Laboratory Press, Cold Spring Harbor, N.Y. (1989). (see in particular Screening By Hybridization 1.90 and Sequencing Denatured Double-Stranded DNA Templates 13.70). Illustrative of the invention, the polynucleotides set out in Table 1 [SEQ ID NO:1, 4 and 5] were discovered in a DNA library derived from Staphylococcus aureus WCUH 294.

Certain DNA sequences set out in Table 1 [SEQ ID NO:1] contains an open reading frame encoding a protein having about the number of amino acid residues set forth in Table 1 [SEQ ID NO:2] with a deduced molecular weight that can be calculated using amino acid residue molecular weight values well known in the art. The polynucleotide of SEQ ID NO:1, between nucleotide number 1 through number 351 encodes the polypeptide of SEQ ID NO:2. The stop codon begins at nucleotide number 352 of SEQ ID NO:1.

RNaseP of the invention is structurally related to other proteins of the RNase P family, as shown by the results of sequencing the DNA encoding RNaseP of the deposited strain. The protein exhibits greatest homology to B. subtilis protein among known proteins. RNaseP of Table 1 [SEQ ID NO:2] has significant identity and similarity over its entire length with the amino acid sequence of B. subtilis RNase P polypeptide.

The invention provides a polynucleotide sequence identical over its entire length to the coding sequence in Table 1 [SEQ ID NO:1]. Also provided by the invention is the coding sequence for the mature polypeptide or a fragment thereof, by itself as well as the coding sequence for the mature polypeptide or a fragment in reading frame with other coding sequence, such as those encoding a leader or secretory sequence, a pre-, or pro- or prepro-protein sequence. The polynucleotide may also contain non-coding sequences, including for example, but not limited to non-coding 5' and 3' sequences, such as the transcribed, non-translated sequences, termination signals, ribosome binding sites, sequences that stabilize mRNA, introns, polyadenylation signals, and additional coding sequence which encode additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al., Proc. Natl. Acad. Sci., USA 86: 821–824 (1989), or an HA tag (Wilson et al., Cell 37: 767 (1984). Polynucleotides of the invention also include, but are not limited to, polynucleotides comprising a structural gene and its naturally associated sequences that control gene expression.

A preferred embodiment of the invention is a polynucleotide of comprising nucleotide 1 to 351 or 354 set forth in SEQ ID NO:1 of Table 1 which encode the RNaseP polypeptide.

The invention also includes polynucleotides of the formula set forth in Table 1 (C)[SEQ ID NO:1 and (F)[SEQ ID NO:3] wherein, at the 5' end of the molecule, X is hydrogen, and at the 3' end of the molecule, Y is hydrogen or a metal, $R_1$ and $R_2$ is any nucleic acid residue, and n is an integer between 1 and 3000. Any stretch of nucleic acid residues denoted by either R group, where R is greater than 1, may be either a heteropolymer or a homopolymer, preferably a heteropolymer. A preferred embodiment for the sequence set forth in Table 1 (F) [SEQ ID NO:3] has $R_1$ or $R_2$ being between 1 and 10 or 1 and 20, and especially being 1, 2, 3, 4, 5, 6, 7, 8, 9 or 10. The invention also provides RNA transcribed from such polynucleotides, particularly catalytic RNAs.

The term "polynucleotide encoding a polypeptide" as used herein encompasses polynucleotides that include a sequence encoding a polypeptide of the invention, particularly a bacterial polypeptide and more particularly a polypeptide of the Staphylococcus aureus RNaseP having the amino acid sequence set out in Table 1 [SEQ ID NO:2]. The term also encompasses polynucleotides that include a single continuous region or discontinuous regions encoding the polypeptide (for example, interrupted by integrated phage or an insertion sequence or editing) together with additional regions, that also may contain coding and/or non-coding sequences.

The invention further relates to variants of the polynucleotides described herein that encode for variants of the polypeptide having the deduced amino acid sequence of Table 1 [SEQ ID NO:2]. Variants that are fragments of the polynucleotides of the invention may be used to synthesize full-length polynucleotides of the invention.

In addition to the standard A, G, C, T/U representations for nucleic acid bases, the term "N" is also used. "N" means that any of the four DNA or RNA bases may appear at such a designated position in the DNA or RNA sequence, except that, in preferred embodiments, N can not be a base that when taken in combination with adjacent nucleotide positions, when read in the correct reading frame, would have the effect of generating a premature termination codon in such reading frame.

Further particularly preferred embodiments are polynucleotides encoding RNaseP variants, that have the amino acid sequence of RNaseP polypeptide of Table 1 [SEQ ID NO:2] in which several, a few, 5 to 10, 1 to 5, 1 to 3, 2, 1 or no amino acid residues are substituted, deleted or added, in any combination. Especially preferred among these are silent substitutions, additions and deletions, that do not alter the properties and activities of RNaseP.

Further preferred embodiments of the invention are polynucleotides that are at least 50%, 60% or 70% identical over their entire length to a polynucleotide encoding RNaseP polypeptide having an amino acid sequence set out in Table 1 [SEQ ID NO:2], and polynucleotides that are complementary to such polynucleotides. Alternatively, most highly preferred are polynucleotides that comprise a region that is at least 80% identical over its entire length to a polynucleotide encoding RNaseP polypeptide of the deposited strain and polynucleotides complementary thereto. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Preferred embodiments of the invention are polynucleotides that are at least 50%, 60% or 70% identical over their entire length to an RNaseP polynucleotide having a nucleotide sequence set out in SEQ ID NO:3, and 4, and polynucleotides that are complementary to such polynucleotides. Alternatively, most highly preferred are polynucleotides that comprise a region that is at least 80% identical over its entire length to an RNaseP polynucleotide of the deposited strain and polynucleotides complementary thereto. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred. It is especially preferred that these polynucleotides be RNAs, especially catalytic RNAs.

Preferred embodiments are polynucleotides that encode polypeptides that retain substantially the same biological function or activity as the mature polypeptide encoded by the DNA of Table 1 [SEQ ID NO:1] or as the RNase P RNA component transcribed by the DNA of SEQ ID NO:3 and 4.

The invention further relates to polynucleotides that hybridize to the herein above-described sequences. In this regard, the invention especially relates to polynucleotides that hybridize under stringent conditions to the herein above-described polynucleotides. As herein used, the terms "stringent conditions" and "stringent hybridization conditions" mean hybridization will occur only if there is at least 95% and preferably at least 97% identity between the sequences. An example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 micrograms/ml denatured, sheared salmon sperm DNA, followed by washing the hybridization support in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein.

The invention also provides a polynucleotide consisting essentially of a polynucleotide sequence obtainable by screening an appropriate library containing the complete gene for a polynucleotide sequence set forth in SEQ ID NO:1 or SEQ ID NO:3 or SEQ ID NO:4 under stringent hybridization conditions with a probe having the sequence of said polynucleotide sequence set forth in SEQ ID NO:1 or SEQ ID NO:3 or SEQ ID NO:4 respectively or a fragment thereof; and isolating said DNA sequence. Fragments useful for obtaining such a polynucleotide include, for example, probes and primers described elsewhere herein.

As discussed herein regarding polynucleotide assays of the invention, for instance, polynucleotides of the invention as discussed above, may be used as a hybridization probe for RNA, cDNA and genomic DNA to isolate full-length cDNAs and genomic clones encoding RNaseP and to isolate cDNA and genomic clones of other genes that have a high sequence similarity to the RNaseP gene. Such probes generally will comprise at least 15 bases. Preferably, such probes will have at least 30 bases and may have at least 50 bases. Particularly preferred probes will have at least 30 bases and will have 50 bases or less.

Polynucleotides of the invention that are oligonucleotides derived from the sequences of SEQ ID NOS:1 and/or 2 and/or 3 and/or 4 may be used in the processes herein as described, but preferably for PCR, to determine whether or not the polynucleotides identified herein in whole or in part are transcribed in bacteria in infected tissue. It is recognized that such sequences will also have utility in diagnosis of the stage of infection and type of infection the pathogen has attained.

The invention also provides polynucleotides that may encode a polypeptide that is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the invention may encode a mature protein, a mature protein plus a leader sequence (which may be referred to as a preprotein), a precursor of a mature protein having one or more prosequences that are not the leader sequences of a preprotein, or a preproprotein, which is a precursor to a proprotein, having a leader sequence and one or more prosequences, which generally are removed during processing steps that produce active and mature forms of the polypeptide.

Cloning of *S. aureus* RNase P RNA Structural Gene

A partial homolog to *B. subtilis* RNase P RNA was identified in a *S. aureus* sequence database comprising sequences from randomly sequenced *S. aureus* DNA library in an *E. coli* host.

A PCR primer based on these data was designed to the 3' end of the gene (primer: 5'-CGC GAA GTG TGT CTC GTT TAT ACG-3' [SEQ ID NO:5] and a second based on a universally conserved sequence within the 5' domain (5'-GAG GAA AGT CCA TGC TC-3') [SEQ ID NO:6] permitted recovery of approximately 90% of the gene. The complete structural gene was amplified using a degenerate primer (5'-$^c/_T$GATAMTC$^G/_T$G$^A/_G$TAA$^T/_C$C-3') [SEQ ID NO:13] that would allow the RNA product to form the predicted helices P1 and P2. The structural gene has been cloned behind a T7 promoter, sequenced and shown to be highly related to *B. subtilis* homolog. The precise *S. aureus* genomic sequence encoding (transcribing) helices P1 and P2 may be determined by skilled artisans using methods and compounds of the invention, such as the degenerate primer described above [SEQ ID NO:131]. The exact 5' end has been determined by primer extension analysis using endogenous *S. aureus* RNA isolated from *S. aureus* WCUH29. The sequence of the first 20 nucleotides of RNaseP RNA 5' end as determined by this primer extension analysis is:

5'-GUUCUGAUAUUUUGGGUAAU-3'[SEQ ID NO:15].

Further Description and Definitions

The coding region of the RNaseP gene may be isolated, for example, by screening using a deposit containing a *Staphylococcus aureus* WCUH 29 strain which has been deposited with the National Collections of Industrial and Marine Bacteria Ltd. (herein "NCIMB"), 23 St. Machar Drive, Aberdeen AB2 1RY, Scotland on Sep. 11, 1995 and assigned NCIMB Deposit No. 40771. It was referred to as *Staphylococcus aureus* WCUH29 on deposit. The *Staphylococcus aureus* strain deposit is referred to herein as "the deposited strain" or as "the DNA of the deposited strain."

The deposited strain contains the full length RNaseP gene. The sequence of the polynucleotides contained in the deposited strain, as well as the amino acid sequence of the polypeptide encoded thereby, are controlling in the event of any conflict with any description of sequences herein.

The deposit of the deposited strain has been made under the terms of the Budapest Treaty on the International Recognition of the Deposit of Micro-organisms for Purposes of Patent Procedure. The strain will be irrevocably and without restriction or condition released to the public upon the issuance of a patent. The deposited strain is provided merely as convenience to those of skill in the art and is not an admission that a deposit is required for enablement, such as that required under 35 U.S.C. §112.

A license may be required to make, use or sell the deposited strain, and compounds derived therefrom, and no such license is hereby granted.

The nucleotide sequences disclosed herein can also be obtained by synthetic chemical techniques known in the art or can be obtained from *S. aureus* WCUH 29 by probing a DNA preparation with probes constructed from the particular sequences disclosed herein. Alternatively, oligonucleotides derived from a disclosed sequence can act as PCR primers in a process of PCR-based cloning of the sequence from a bacterial genomic source. It is recognized that such sequences will also have utility in diagnosis of the type of infection the pathogen has attained.

A polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the polypeptide may be identical to the coding sequence shown or may be a different coding sequence which coding sequence, as a result of the redundancy or degeneracy of the genetic code, encoding the same polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention therefore includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and a presequence (leader sequence). Further, the amino acid sequences provided herein show a methionine residue at the $NH_2$-terminus. It is appreciated, however, that during post-translational modification of the peptide, this residue may be deleted. Accordingly, this invention contemplates the use of both the methionine-containing and the methionineless amino terminal variants of each protein disclosed herein.

The polynucleotides of the present invention may also have the coding sequence fused in frame to a marker sequence at either the 5' or 3' terminus of the gene which allows for purification of the polypeptide of the present invention. The marker sequence may be a hexa-histidine tag supplied by the pQE series of vectors (supplied commercially by Quiagen Inc.) to provide for purification of the polypeptide fused to the marker in the case of a bacterial host. Alternatively the maltose binding protein (MBP) fusion system may be employed. In this system the gene of interest is fused the malE gene encoding the MBP (supplied by New England BioLabs). The fusion product is purified in a one step procedure based on the MBP affinity for maltose. A pre-engineered Xa cleavage site allows for efficient removal of the MBP component from the gene product of interest.

In order to facilitate understanding of the following example certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on an agarose gel to isolate the desired fragment. Size separation of the cleaved fragments is generally performed using a 1% percent agarose gel.

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., supra., p. 146). Unless otherwise provided, ligation may be accomplished using known buffers and conditions with 10 units to T4 DNA ligase ("ligase") per 0.5 μg of approximately equimolar amounts of the DNA fragments to be ligated.

The polypeptides and polynucleotides of the present invention are preferably provided in an isolated form, and preferably are purified to homogeneity.

A "replicon" is any genetic element (e.g., plasmid, chromosome, virus) that functions as an autonomous unit of DNA replication in vivo; i.e., capable of replication under its own control.

A "vector" is a replicon, such as a plasmid, phage, or cosmid, to which another DNA segment may be attached so as to bring about the replication of the attached segment.

A "double-stranded DNA molecule" refers to the polymeric form of deoxyribonucleotides (bases adenine, guanine, thymine, or cytosine) in a double-stranded helix, both relaxed and supercoiled. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having the sequence homologous to the mRNA).

A DNA "coding sequence of" or a "nucleotide sequence encoding" a particular protein, is a DNA sequence which is transcribed and translated into a polypeptide when placed under the control of appropriate regulatory sequences.

A "promoter sequence" is a DNA regulatory region capable of binding RNA polymerase in a cell and initiating transcription of a downstream (3' direction) coding sequence. For purposes of defining the present invention, the promoter sequence is bound at the 3' terminus by a translation start codon (e.g., ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain the −10 and −35 consensus sequences.

DNA "control sequences" refers collectively to promoter sequences, ribosome binding sites, polyadenylation signals, transcription termination sequences, upstream regulatory domains, enhancers, and the like, which collectively provide for the expression (i.e., the transcription and translation) of a coding sequence in a host cell.

A control sequence "directs the expression" of a coding sequence in a cell when RNA polymerase will bind the promoter sequence and transcribe the coding sequence into mRNA, which is then translated into the polypeptide encoded by the coding sequence.

A "host cell" is a cell which has been transformed or transfected, or is capable of transformation or transfection by an exogenous DNA sequence.

A cell has been "transformed" by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to eukaryotic cells, a stably transformed or transfected cell is one in which the exogenous DNA has become integrated into the chromosome so that it is inherited by daughter cells through chromosome replication. This stability is demonstrated by the ability of the eukaryotic cell to establish cell lines or clones comprised of a population of daughter cell containing the exogenous DNA.

A "clone" is a population of cells derived from a single cell or common ancestor by mitosis. A "cell line" is a clone of a primary cell that is capable of stable growth in vitro for many generations.

A "heterologous" region of a DNA construct is an identifiable segment of DNA within or attached to another DNA molecule that is not found in association with the other molecule in nature.

Preparation of the RNase P Protein Component

The present invention also relates to vectors which include polynucleotides of the present invention, host cells which are genetically engineered with vectors of the invention and the production of polypeptides of the invention by recombinant techniques.

In accordance with yet a further aspect of the present invention, there is therefore provided a process for producing the polypeptide of the invention by recombinant techniques by expressing a polynucleotide encoding said polypeptide in a host and recovering the expressed product. Alternatively, the polypeptides of the invention can be synthetically produced by conventional peptide synthesizers.

Host cells are genetically engineered (transduced or transformed or transfected) with the vectors of this invention which may be, for example, a cloning vector or an expression vector. The vector may be, for example, in the form of a plasmid, a cosmid, a phage, etc. The engineered host cells can be cultured in conventional nutrient media modified as appropriate for activating promoters, selecting transformants or amplifying the genes. The culture conditions, such as temperature, pH and the like, are those previously used with the host cell selected for expression, and will be apparent to the ordinarily skilled artisan.

Suitable expression vectors include chromosomal, non-chromosomal and synthetic DNA sequences, e.g., bacterial plasmids; phage DNA; baculovirus; yeast plasmids; vectors derived from combinations of plasmids and phage DNA. However, any other vector may be used as long as it is replicable and viable in the host.

For recombinant production, host cells can be genetically engineered to incorporate expression systems or portions thereof or polynucleotides of the invention. Introduction of a polynucleotide into the host cell can be effected by methods described in many standard laboratory manuals, such as Davis et al., BASIC METHODS IN MOLECULAR BIOLOGY, (1986) and Sambrook et al., MOLECULAR CLONING: A LABORATORY MANUAL, 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, transduction, scrape loading, ballistic introduction and infection.

Representative examples of appropriate hosts include bacterial cells, such as streptococci, staphylococci, enterococci *E. coli*, streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, 293 and Bowes melanoma cells; and plant cells.

A great variety of expression systems can be used to produce the polypeptides of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., MOLECULAR CLONING, A LABORATORY MANUAL, (supra).

The appropriate DNA sequence may be inserted into the vector by a variety of procedures. In general, the DNA sequence is inserted into an appropriate restriction endonuclease site(s) by procedures known in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli*. lac or trp, the phage lambda $P_L$ promoter and other promoters known to control expression of genes in eukaryotic or prokaryotic cells or their viruses. The expression vector may also contains a ribosome binding site for translation initiation and/or a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence may or may not contain a signal peptide or leader sequence. The polypeptides of the present invention can be expressed using, for example, the *E. coli* tac promoter or the protein A gene (spa) promoter and signal sequence. Leader sequences can be removed by the bacterial host in post-translational processing. See, e.g., U.S. Pat. Nos. 4,431,739; 4,425,437; 4,338,397. Promoter regions can be selected from any desired gene using CAT (chloramphenicol transferase) vectors or other vectors with selectable markers. Two appropriate vectors are PKK232–8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In addition to control sequences, it may be desirable to add regulatory sequences which allow for regulation of the expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the coding sequences may be desirable to achieve this end. For example, in some cases it may be necessary to modify the sequence so that it may be attached to the control sequences with the appropriate orientation; i.e., to maintain the reading frame. The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

The vector containing the appropriate DNA sequence as hereinabove described, as well as an appropriate promoter or control sequence, may be employed to transform an appropriate host to permit the host to express the protein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pET-3 vectors (Stratagene), pQE70, pQE60, pQE-9 (Qiagen), pbs, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pBlueBacIII (Invitrogen), pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Examples of recombinant DNA vectors for cloning and host cells which they can transform include the bacteriophage λ (E. coli), pBR322 (E. coli), pACYC177 (E. coli), pKT230 (gram-negative bacteria), pGV1106 (gram-negative bacteria), pLAFRI (gram-negative bacteria), pME290 (non-E. coli gram-negative bacteria), pHV14 (E. coli and Bacilluis subtilis), pBD9 (Bacillus), pIJ61 (Streptomyces), pUC6 (Streptomyces), YIp5 (Saccharomyces), a baculovirus insect cell system, YCp 19 (Saccharomyces). See, generally, "DNA Cloning": Vols. I & II, Glover et al. ed. IRL Press Oxford (1985) (1987) and; T. Maniatis et al. ("Molecular Cloning" Cold Spring Harbor Laboratory (1982).

In some cases, it may be desirable to add sequences which cause the secretion of the polypeptide from the host organism, with subsequent cleavage of the secretory signal.

Polypeptides can be expressed in host cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Depending on the expression system and host selected, the polypeptide of the present invention may be produced by growing host cells transformed by an expression vector described above under conditions whereby the polypeptide of interest is expressed. The polypeptide is then isolated from the host cells and purified. If the expression system secretes the polypeptide into growth media, the polypeptide can be purified directly from the media. If the polypeptide is not secreted, it is isolated from cell lysates or recovered from the cell membrane fraction. Where the polypeptide is localized to the cell surface, whole cells or isolated membranes can be used as an assayable source of the desired gene product. Polypeptide expressed in bacterial hosts such as E. coli may require isolation from inclusion bodies and refolding. Where the mature protein has a very hydrophobic region which leads to an insoluble product of overexpression, it may be desirable to express a truncated protein in which the hydrophobic region has been deleted. The selection of the appropriate growth conditions and recovery methods are within the skill of the art.

The polypeptide can be recovered and purified from recombinant cell cultures by methods including ammonium sulphate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

Depending upon the host employed in a recombinant production procedure, the polypeptides of the present invention may be glycosylated or may be non-glycosylated. Polypeptides of the invention may also include an initial methionine amino acid residue.

Preparation of the RNase P RNA Component

The RNase P RNA molecules are prepared by run-off in vitro transcription using T7 RNA polymerase as according to standard conditions—usually as recommended by the supplier, e.g., Promega. The plasmid is linearized with an appropriate restriction enzyme generating a linear dsDNA comprising the full length gene encoding the RNase PRNA. The RNA is purified either from a preparative denaturing acrylamide gel or is precipitated prior to use in in vitro cleavage assays. The substrates for the RNase P RNA and the RNA complexed with its protein (RNase P protein) can be obtained by in vitro transcription of cloned genes. Useful substrates included but are not limited to pre-tRNA$^{Met}$ or E.

coli or B. subtilis pre-4.5S molecules and may be expressed using an in vitro transcription system directed by T7 RNA polymerase as described above. The RNA can also be prepared by automated synthesis.

Antazonists and Agonists—Assays and Molecules

This invention provides a method of screening drugs to identify those which interfere with the RNA portion, the protein portion and/ or the intact RNA/protein complex of the RNase P described herein, which method comprises measuring the interference of the activity of the protein and/or RNA by a test drug. For example since the RNA portion selected has a catalytic activity, after suitable purification and formulation the activity of the RNA can be followed by its ability to convert its natural or synthetic RNA substrates. By incorporating different chemically synthesized test compounds or natural products into such an assay of enzymatic activity one is able to detect those additives which compete with the natural or synthetic substrate or otherwise inhibit enzymatic activity.

Polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See, e.g., Coligan et al., *Current Protocols in Immunology* 1(2): Chapter 5 (1991).

The invention also provides a method of screening compounds to identify those which enhance (agonist) or block (antagonist) the action of RNaseP polypeptides or polynucleotides, particularly those compounds that are bacteriostatic and/or bacteriocidal. The method of screening may involve high-throughput techniques. For example, to screen for agonists or antagonists, a synthetic reaction mix, a cellular compartment, such as a membrane, cell envelope or cell wall, or a preparation of any thereof, comprising RNaseP polypeptide and a labeled substrate or ligand of such polypeptide is incubated in the absence or the presence of a candidate molecule that may be a RNaseP agonist or antagonist. The ability of the candidate molecule to agonize or antagonize the RNaseP polypeptide is reflected in decreased binding of the labeled ligand or decreased production of product from such substrate. Molecules that bind gratuitously, i.e., without inducing the effects of RNaseP polypeptide are most likely to be good antagonists. Molecules that bind well and increase the rate of product production from substrate are agonists. Detection of the rate or level of production of product from substrate may be enhanced by using a reporter system. Reporter systems that may be useful in this regard include but are not limited to colorimetric labeled substrate converted into product, a reporter gene that is responsive to changes in RNaseP polynucleotide or polypeptide activity, and binding assays known in the art.

Another example of an assay for RNaseP antagonists is a competitive assay that combines RNaseP and a potential antagonist with RNaseP-binding molecules, recombinant RNaseP binding molecules, natural substrates or ligands, or substrate or ligand mimetics, under appropriate conditions for a competitive inhibition assay. RNaseP can be labeled, such as by radioactivity or a colorimetric compound, such that the number of RNaseP molecules bound to a binding molecule or converted to product can be determined accurately to assess the effectiveness of the potential antagonist.

Potential antagonists include small organic molecules, peptides, polypeptides and antibodies that bind to a polynucleotide or polypeptide of the invention and thereby inhibit or extinguish its activity. Potential antagonists also may be small organic molecules, a peptide, a polypeptide such as a closely related protein or antibody that binds the same sites on a binding molecule, such as a binding molecule, without inducing RNaseP-induced activities, thereby preventing the action of RNaseP by excluding RNaseP from binding.

Potential antagonists include a small molecule that binds to and occupies the binding site of the polypeptide thereby preventing binding to cellular binding molecules, such that normal biological activity is prevented. Examples of small molecules include but are not limited to small organic molecules, peptides or peptide-like molecules. Other potential antagonists include antisense molecules (see Okano, *J. Neurochem.* 56: 560 (1991); *OLIGODEOXYNUCLEOTIDES AS ANTISENSE INHIBITORS OF GENE EXPRESSION*, CRC Press, Boca Raton, Fla. (1988), for a description of these molecules). Preferred potential antagonists include compounds related to and variants of RNaseP.

Each of the DNA sequences provided herein may be used in the discovery and development of antibacterial compounds. The encoded protein, upon expression, can be used as a target for the screening of antibacterial drugs. Additionally, the DNA sequences encoding the amino terminal regions of the encoded protein or Shine-Delgarno or other translation facilitating sequences of the respective mRNA can be used to construct antisense sequences to control the expression of the coding sequence of interest.

The invention also provides the use of the polypeptide, polynucleotide or inhibitor of the invention to interfere with the initial physical interaction between a pathogen and mammalian host responsible for sequelae of infection. In particular the molecules of the invention may be used: in the prevention of adhesion of bacteria, in particular gram positive bacteria, to mammalian extracellular matrix proteins on in-dwelling devices or to extracellular matrix proteins in wounds; to block RNaseP protein-mediated mammalian cell invasion by, for example, initiating phosphorylation of mammalian tyrosine kinases (Rosenshine et al., *Infect. Immun.* 60:2211 (1992); to block bacterial adhesion between mammalian extracellular matrix proteins and bacterial RNaseP proteins that mediate tissue damage and; to block the normal progression of pathogenesis in infections initiated other than by the implantation of in-dwelling devices or by other surgical techniques.

The antagonists and agonists of the invention may be employed, for instance, to inhibit and treat disease, such as, infections of the upper respiratory tract (e.g., otitis media, bacterial tracheitis, acute epiglottitis, thyroiditis), lower respiratory (e.g., empyema, lung abscess), cardiac (e.g., infective endocarditis), gastrointestinal (e.g., secretory diarrhoea, splenic absces, retroperitoneal abscess), CNS (e.g., cerebral abscess), eye (e.g., blepharitis, conjunctivitis, keratitis, endophthalmitis, preseptal and orbital cellulitis, darcryocystitis), kidney and urinary tract (e.g., epididymitis, intrarenal and perinephric absces, toxic shock syndrome), skin (e.g., impetigo, folliculitis, cutaneous abscesses, cellulitis, wound infection, bacterial myositis) bone and joint (e.g., septic arthritis, osteomyelitis).

HTP Screening Strateoies

Assays can be developed to detect compounds that inhibit RNase P directed cleavage of RNA substrates. Several possible assay formats are suitable for HTP screening based upon the ability to incorporate labels within the RNA in a site-specific fashion by chemical synthesis. The conventional radioactive-based format is preferred, while a homogeneous fluorescence-based format is useful for subsequent follow-up of lead compounds. The use of both formats is contemplated by this invention.

Functional RNase P Assay

Biotin is introduced in to an appropriate position within the RNA substrate and the 5' terminus labeled with $^{32}$P. The substrate is linked via streptavidin within a 96-well plate. Following RNase P dependent hydrolysis of the substrate, the radiolabelled 5' leader cleavage product is released into the bulk solution phase, and subject to scintillation counting. Alternatively, the RNA substrate is bound to a streptavidin-coated flashplate such that the release of the radioactive 6-mer into the solution phase results in a decrease in signal. This has the advantage that it is a homogeneous, continuous assay format and requires no additional manipulations after starting the assay. Both formats are useful in the practice of this invention because they use the same RNA substrate.

RNA Fragment Library Rescue

An effective approach for identifying compounds that interact with RNA is contemplated. The concept is based on the over-expression of a drug binding site that is recreated on an RNA fragment, which will sequester the drug and permit the continued functioning of the intact ribozyme. This approach has recently been described in the context of a search for ligands that bind ribosomal RNA (Howard, B-A, et al. *Biochem. Cell Bio.* 73(11/12): 1161–1166 (1995)). Following selection the random RNA fragments that apparently present a minimal target structure for drug recognition, are incorporated into a protocol for rational drug design. Accordingly, random fragment libraries based on M1 RNA will be generated and used in HTP screening to identify compounds that disrupt RNA/protein interaction.

Cyclic Peptide Phage Libraries

The incorporation of conformational constraints into flexible lead compounds is a powerful strategy to increase lead potency and is particularly useful in the field of peptidomimetic design.( Al-Obeidi, F. et al., *J. Med. Chem.* 32: 2555–2561(1989);Barker, P. L., et al., *J. Med. Chem.* 35: 2040–2048 (1992)). Cyclization has been shown to increase the propensity for beta-turn formation in peptides the potential of which has been demonstrated by the identification of high-affinity ligands for streptavidin (Lee, M. S., et al., *FEBS Lett.* 359: 113–118 (1995)).

In this case, cyclic peptide libraries were constructed with flanking cysteine residues to allow efficient disulfide bond formation and cyclization during phage assembly. The streptavidin bound crystal structures of two disulfide bridged cyclic peptides showed both peptides to be in beta-turn conformations (Kahn, M. (Guest, Ed., 1993) *Tetrahedron* 49, Symp. 50, 3433–3677).

Beta-turns are key recognition elements in many biological interactions therefore effort has been focused on the design of small constrained beta-turn mimics (Kahn, M. (Guest Ed., 1993) *Tetrahedron* 49, Symp. 50, 3433–3677). This approach, when applied to RNase P, could identify cyclic peptides suitable for peptide mimic synthesis as inhibitor molecules. A cyclic octapeptide phage display library may be constructed and used to identify peptides that interact with defined RNA domains.

Secondary Evaluation

SELEX: Systematic Evolution of Ligands by Exponential Enrichment:

This approach may be employed in an attempt to identify RNA recognition motifs for RNase P RNA (M1 RNA) protein binding for structural analysis as an aid to rational drug design and the secondary evaluation of compounds identified via the HTP screens. The technology is based on the repeated selection and amplification of RNA fragments that specifically bind to a protein with high affinities (Szostak, J. W., TIBS 17: 89–93 (1992)). Fragment libraries based on the *S. aureus* and *E. coli* RNase P RNAs may be constructed for the in vitro synthesis of RNA fragments and the subsequent selection of molecules that bind their respective proteins. Chemical and enzymatic structure probing technologies may be employed in combination with protein/RNA protection studies to map the interactive sites. SELEX based on the resulting RNA fragment(s) may be further exploited to determine the minimal structural requirements for RNA recognition.

Disruption of RNase P Assembly

The identification of a protein/RNA-fragment pair permits the development of a screen for compounds that disrupt their assembly. Drug induced disruption of labeled RNA bound to immobilized protein (biotin/streptavidin) would result in the concomitant decrease/loss of the signal generated by the presence of the RNA.

RNA/Drug Interactions

RNase P RNA fragments that confer drug resistance (RNA Fragment Rescue Library supra) may be sequenced and expressed in vitro for chemical and enzymatic structure probing in the presence and absence of the drug in an attempt to map the binding site. SELEX may be applied to lead compounds in an attempt to identify the minimal structural requirements for drug binding.

RNase P Substrates

Minimal RNA substrates may be chemically synthesized for HTP screening including both pre-tRNA and pre-4.5S RNA derivatives. RNA-ligand interactions involving ribose 2'-hydroxyl groups of specific nucleotides may be probed via chemical synthesis of the appropriately modified RNA fragment. In order to retain the $C^3$-endo configuration characteristic of ribonucleotides, 2'-methoxy and 2'-fluororibonucleotides analogues can be used, the latter being preferred on steric grounds. Nucleotides lacking a 2'-substituent adopt the undesired $C^2$-endo configuration.

The invention also relates to inhibitors identified by any of the techniques described herein. Because of the enzymatic nature of RNase P action, it is appreciated that inhibitors may be identified which act as transition state mimics, inhibitors of product release or inhibitors of substrate binding.

Diagnostic Assays

This invention is also related to the use of the RNaseP polynucleotides of the invention for use as diagnostic reagents. Detection of RNaseP in a eukaryote, particularly a mammal, and especially a human, will provide a diagnostic method for diagnosis of a disease. Eukaryotes (herein also "individual(s)"), particularly mammals, and especially humans, infected with an organism comprising the RNaseP gene may be detected at the nucleic acid level by a variety of techniques.

Nucleic acids for diagnosis may be obtained from an infected individual's cells and tissues, such as bone, blood, muscle, cartilage, and skin. Genomic DNA may be used directly for detection or may be amplified enzymatically by using PCR or other amplification technique prior to analysis. RNA or cDNA may also be used in the same ways. Using amplification, characterization of the species and strain of prokaryote present in an individual, may be made by an analysis of the genotype of the prokaryote gene. Deletions and insertions can be detected by a change in size of the amplified product in comparison to the genotype of a reference sequence. Point mutations can be identified by hybridizing amplified DNA to labeled RNaseP polynucleotide sequences. Perfectly matched sequences can be distinguished from mismatched duplexes by RNase digestion or by differences in melting temperatures. DNA sequence differences may also be detected by alterations in the electrophoretic mobility of the DNA fragments in gels, with or without denaturing agents, or by direct DNA sequencing. See, e.g., Myers et al., *Science*, 230: 1242 (1985). Sequence changes at specific locations also may be revealed by nuclease protection assays, such as RNase and SI protection or a chemical cleavage method. See, e.g., Cotton et al., *Proc. Natl. Acad. Sci., USA*, 85: 43974401 (1985).

Cells carrying mutations or polymorphisms in the gene of the invention may also be detected at the DNA level by a variety of techniques, to allow for serotyping, for example. For example, RT-PCR can be used to detect mutations. It is particularly preferred to used RT-PCR in conjunction with automated detection systems, such as, for example, GeneScan. RNA or cDNA may also be used for the same purpose, PCR or RT-PCR. As an example, PCR primers complementary to a nucleic acid encoding RNaseP can be used to identify and analyze mutations. Examples of representative primers are shown in the Examples. The invention further provides these primers with 1, 2, 3 or 4 nucleotides removed from the 5' and/or the 3' end. These primers may be used for, among other things, amplifying RNaseP DNA isolated from a sample derived from an individual. The primers may be used to amplify the gene isolated from an infected individual such that the gene may then be subject to various techniques for elucidation of the DNA sequence. In this way, mutations in the DNA sequence may be detected and used to diagnose infection and to serotype and/or classify the infectious agent.

The invention further provides a process for diagnosing, disease, preferably bacterial infections, more preferably infections by *Staphylococcus aureus*, and most preferably disease, such as, infections of the upper respiratory tract (e.g., otitis media, bacterial tracheitis, acute epiglottitis, thyroiditis), lower respiratory (e.g., empyema, lung abscess), cardiac (e.g., infective endocarditis), gastrointestinal (e.g., secretory diarrhoea, splenic absces, retroperitoneal abscess), CNS (e.g., cerebral abscess), eye (e.g., blepharitis, conjunctivitis, keratitis, endophthalmitis, preseptal and orbital cellulitis, darcryocystitis), kidney and urinary tract (e.g., epididymitis, intrarenal and perinephric absces, toxic shock syndrome), skin (e.g., impetigo, folliculitis, cutaneous abscesses, cellulitis, wound infection, bacterial myositis) bone and joint (e.g., septic arthritis, osteomyelitis), comprising determining from a sample derived from an individual a increased level of expression of polynucleotide having the sequence of Table 1 [SEQ ID NO: 1]. Increased or decreased expression of RNaseP polynucleotide can be measured using any on of the methods well known in the art for the quantitation of polynucleotides, such as, for example, amplification, PCR, RT-PCR, RNase protection, Northern blotting and other hybridization methods.

In addition, a diagnostic assay in accordance with the invention for detecting over-expression of RNaseP protein compared to normal control tissue samples may be used to detect the presence of an infection, for example. Assay techniques that can be used to determine levels of a RNaseP protein, in a sample derived from a host are well-known to those of skill in the art. Such assay methods include radioimmunoassay, competitive-binding assays, Western Blot analysis and ELISA assays.

Antibodies

The polypeptides of the invention or variants thereof, or cells expressing them can be used as an immunogen to produce antibodies immunospecific for such polypeptides. "Antibodies" as used herein includes monoclonal and polyclonal antibodies, chimeric, single chain, simianized antibodies and humanized antibodies, as well as Fab fragments, including the products of an Fab immunolglobulin expression library.

The Fab fragment may also be prepared from its parent monoclonal antibody by enzyme treatment, for example using papain to cleave the Fab portion from the Fc portion.

Antibodies generated against the polypeptides of the invention can be obtained by administering the polypeptides or epitope-bearing fragments, analogues or cells to an animal, preferably a nonhuman, using routine protocols. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide. For preparation of monoclonal antibodies, any technique known in the art that provides antibodies produced by continuous cell line cultures can be used. Examples include various techniques, such as those in Kohler, G. and Milstein, C., *Nature* 256: 495–497 (1975); Kozbor et al., *Immunology Today* 4: 72 (1983); Cole et al., pg. 77–96 in *MONOCLONAL ANTIBODIES AND CANCER THERAPY*, Alan R. Liss, Inc. (1985), )), and the EBV-hybridoma technique to produce human monoclonal antibodies; (Cole, et al., 1985, in Monoclonal Antibodies and Cancer Therapy, Alan R. Liss, Inc., pp. 77–96).

The hybridomas are screened to select a cell line with high binding affinity and favorable cross reaction with other staphylococcal species using one or more of the original polypeptide and/or the fusion protein. The selected cell line is cultured to obtain the desired Mab.

Techniques for the production of single chain antibodies (U.S. Pat. No. 4,946,778) can be adapted to produce single chain antibodies to polypeptides of this invention. Also, transgenic mice, or other organisms such as other mammals, may be used to express humanized antibodies.

Alternatively phage display technology may be utilized to select antibody genes with binding activities towards the polypeptide either from repertoires of PCR amplified v-genes of lymphocytes from humans screened for possessing anti-RNaseP or from naive libraries (McCafferty, J. et al., (1990), Nature 348, 552–554; Marks, J. et al., (1992) Biotechnology 10, 779–783). The affinity of these antibodies can also be improved by chain shuffling (Clackson, T. et al., (1991) Nature 352, 624–628).

The antibody should be screened again for high affinity to the polypeptide and/or fusion protein.

As mentioned above, a fragment of the final antibody may be prepared.

The antibody may be either intact antibody of $M_r$ approx 150,000 or a derivative of it, for example a Fab fragment or a Fv fragment as described in Skerra, A and Pluckthun, A., *Science* 240:1038–1040 (1988). If two antigen binding domains are present each domain may be directed against a different epitope—termed 'bispecific' antibodies.

If two antigen binding domains are present each domain may be directed against a different epitope—termed 'bispecific' antibodies.

In particular derivatives which are slightly longer or slightly shorter than the native protein or polypeptide fragment of the present invention may be used. In addition, polypeptides in which one or more of the amino acid residues are modified may be used. Such peptides may, for example, be prepared by substitution, addition, or rearrangement of amino acids or by chemical modification thereof. All such substitutions and modifications are generally well known to those skilled in the art of peptide chemistry.

The above-described antibodies may be employed to isolate or to identify clones expressing the polypeptides to purify the polypeptides by affinity chromatography.

Thus, among others, antibodies against RNaseP- polypeptide may be employed to treat infections, particularly bacterial infections and especially disease, such as, infections of the upper respiratory tract (e.g., otitis media, bacterial tracheitis, acute epiglottitis, thyroiditis), lower respiratory (e.g., empyema, lung abscess), cardiac (e.g., infective endocarditis), gastrointestinal (e.g., secretory diarrhoea, splenic absces, retroperitoneal abscess), CNS (e.g., cerebral abscess), eye (e.g., blepharitis, conjunctivitis, keratitis, endophthalmitis, preseptal and orbital cellulitis, darcryocystitis), kidney and urinary tract (e.g., epididymitis, intrarenal and perinephric absces, toxic shock syndrome), skin (e.g., impetigo, folliculitis, cutaneous abscesses, cellulitis, wound infection, bacterial myositis) bone and joint (e.g., septic arthritis, osteomyelitis).

Preferably the antibody is prepared by expression of a DNA polymer encoding said antibody in an appropriate expression system such as described above for the expression of polypeptides of the invention. The choice of vector for the expression system will be determined in part by the host, which may be a prokaryotic cell, such as *E. coli* (preferably strain B) or Streptomyces sp. or a eukaryotic cell, such as a mouse C127, mouse myeloma, human HeLa, Chinese hamster ovary, filamentous or unicellular fungi or insect cell. The host may also be a transgenic animal or a transgenic plant (for example, as described in Hiatt, A. et al., *Nature* 340:76–78(1989). Suitable vectors include plasmids, bacteriophages, cosmids and recombinant viruses, derived from, for example, baculoviruses and vaccinia.

Polypeptide variants include antigenically, epitopically or immunologically equivalent variants that form a particular aspect of this invention. The term "antigenically equivalent derivative" as used herein encompasses a polypeptide or its equivalent which will be specifically recognized by certain antibodies which, when raised to the protein or polypeptide according to the invention, interfere with the immediate physical interaction between pathogen and mammalian host. The term "immunologically equivalent derivative" as used herein encompasses a peptide or its equivalent which when used in a suitable formulation to raise antibodies in a vertebrate, the antibodies act to interfere with the immediate physical interaction between pathogen and mammalian host.

The polypeptide, such as an antigenically or immunologically equivalent derivative or a fusion protein thereof is used as an antigen to immunize a mouse or other animal such as a rat or chicken. The fusion protein may provide stability to the polypeptide. The antigen may be associated, for example by conjugation, with an immunogenic carrier protein for example bovine serum albumin (BSA) or keyhole limpet haemocyanin (KLH). Alternatively a multiple antigenic peptide comprising multiple copies of the protein or polypeptide, or an antigenically or immunologically equivalent polypeptide thereof may be sufficiently antigenic to improve immunogenicity so as to obviate the use of a carrier.

Preferably, the antibody or variant thereof is modified to make it less immunogenic in the individual. For example, if the individual is human the antibody may most preferably be "humanized"; where the complimentarity determining region(s) of the hybridoma-derived antibody has been transplanted into a human monoclonal antibody , for example as described in Jones, P. et al. (1986), *Nature* 321, 522–525 or Tempest et al., (1991) *Biotechnology* 9, 266–273. The humanized monoclonal antibody, or its fragment having binding activity, form a particular aspect of this invention.

The modification need not be restricted to one of "humanization"; other primate sequences (for example Newman, R. et al., *Biotechnology* 10: 1455–1460 (1992)) may also be used.

The use of a polynucleotide of the invention in genetic immunization will preferably employ a suitable delivery method such as direct injection of plasmid DNA into muscles (Wolff et al., Hum Mol Genet 1992, 1:363, Manthorpe et al., Hum. Gene Ther. 1963:4, 419), delivery of DNA complexed with specific protein carriers (Wu et al., *J Biol Chem*. 1989: 264,16985), coprecipitation of DNA with calcium phosphate (Benvenisty & Reshef, *PNAS USA*, 1986:83,9551), encapsulation of DNA in various forms of liposomes (Kaneda et al., *Science* 1989:243,375), particle bombardment (Tang et al., *Nature* 1992, 356:152, Eisenbraun et al., *DNA Cell Biol* 1993, 12:791) and in vivo infection using cloned retroviral vectors (Seeger et al., *PNAS USA* 1984:81,5849).

Vaccines

Another aspect of the invention relates to a method for inducing an immunological response in an individual, particularly a mammal which comprises inoculating the individual with RNaseP, or a fragment or variant thereof, adequate to produce antibody and/or T cell immune response to protect said individual from infection, particularly bacterial infection and most particularly *Staphylococcus aureus* infection. Also provided are methods whereby such immunological response slows bacterial replication. Yet another aspect of the invention relates to a method of inducing immunological response in an individual which comprises delivering to such individual a nucleic acid vector to direct expression of RNaseP, or a fragment or a variant thereof, for expressing RNaseP, or a fragment or a variant thereof in vivo in order to induce an immunological response, such as, to produce antibody and/ or T cell immune response, including, for example, cytokine-producing T cells or cytotoxic T cells, to protect said individual from disease, whether that disease is already established within the individual or not. One way of administering the gene is by accelerating it into the desired cells as a coating on particles or otherwise. Such nucleic acid vector may comprise DNA, RNA, a modified nucleic acid, or a DNA/RNA hybrid.

A further aspect of the invention relates to an immunological composition which, when introduced into an individual capable or having induced within it an immunological response, induces an immunological response in such individual to a RNaseP or protein coded therefrom, wherein the composition comprises a recombinant RNaseP or protein coded therefrom comprising DNA which codes for and expresses an antigen of said RNaseP or protein coded therefrom. The immunological response may be used therapeutically or prophylactically and may take the form of antibody immunity or cellular immunity such as that arising from CTL or CD4+T cells.

A RNaseP polypeptide or a fragment thereof may be fused with co-protein which may not by itself produce antibodies, but is capable of stabilizing the first protein and producing a fused protein which will have immunogenic and protective properties. Thus fused recombinant protein, preferably further comprises an antigenic co-protein, such as lipoprotein D from *Haemophilus influenzae*, Glutathione-S-transferase (GST) or beta-galactosidase, relatively large co-proteins which solubilize the protein and facilitate production and purification thereof. Moreover, the co-protein may act as an adjuvant in the sense of providing a generalized stimulation of the immune system. The co-protein may be attached to either the amino or carboxy terminus of the first protein.

Provided by this invention are compositions, particularly vaccine compositions. and methods comprising the polypeptides or polynucleotides of the invention and immunostimulatory DNA sequences, such as those described in Sato, Y. et al. Science 273:352 (1996).

Also, provided by this invention are methods using the described polynucleotide or particular fragments thereof which have been shown to encode non-variable regions of bacterial cell surface proteins in DNA constructs used in such genetic immunization experiments in animal models of infection with *Staphylococcus aureus* will be particularly useful for identifying protein epitopes able to provoke a prophylactic or therapeutic immune response. It is believed that this approach will allow for the subsequent preparation of monoclonal antibodies of particular value from the requisite organ of the animal successfully resisting or clearing infection for the development of prophylactic agents or therapeutic treatments of bacterial infection, particularly *Staphylococcus aureus* infection, in mammals, particularly humans.

The polypeptide may be used as an antigen for vaccination of a host to produce specific antibodies which protect against invasion of bacteria, for example by blocking adherence of bacteria to damaged tissue. Examples of tissue damage include wounds in skin or connective tissue caused, e.g., by mechanical, chemical or thermal damage or by implantation of indwelling devices, or wounds in the mucous membranes, such as the mouth, mammary glands, urethra or vagina.

The invention also includes a vaccine formulation which comprises an immunogenic recombinant protein of the invention together with a suitable carrier. Since the protein may be broken down in the stomach, it is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteriostats and solutes which render the formulation insotonic with the bodily fluid, preferably the blood, of the individual; and aqueous and non-aqueous sterile suspensions which may include suspending agents or thickening agents. The formulations may be presented in unit-dose or multi-dose containers, for example, sealed ampules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

While the invention has been described with reference to certain RNaseP protein, it is to be understood that this covers fragments of the naturally occurring protein and similar proteins with additions, deletions or substitutions which do not substantially affect the immunogenic properties of the recombinant protein.

Compositions, Kits and Administration

The invention also relates to compositions comprising the polynucleotide or the polypeptides discussed above or their agonists or antagonists. The polypeptides of the invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration. The invention further relates to diagnostic and pharmaceutical packs and kits comprising one or more containers filled with one or more of the ingredients of the aforementioned compositions of the invention.

Polypeptides and other compounds of the invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

In therapy or as a prophylactic, the active agent may be administered to an individual as an injectable composition, for example as a sterile aqueous dispersion, preferably isotonic.

Alternatively the composition may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

In-dwelling devices include surgical implants, prosthetic devices and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, continuous ambulatory peritoneal dialysis (CAPD) catheters.

The composition of the invention may be administered by injection to achieve a systemic effect against relevant bacteria shortly before insertion of an in-dwelling device. Treatment may be continued after surgery during the in-body time of the device. In addition, the composition could also be used to broaden perioperative cover for any surgical technique to prevent bacterial wound infections, especially *Staphylococcus aureus* wound infections.

Many orthopaedic surgeons consider that humans with prosthetic joints should be considered for antibiotic prophylaxis before dental treatment that could produce a bacteremia. Late deep infection is a serious complication sometimes leading to loss of the prosthetic joint and is accompanied by significant morbidity and mortality. It may therefore be possible to extend the use of the active agent as a replacement for prophylactic antibiotics in this situation.

In addition to the therapy described above, the compositions of this invention may be used generally as a wound treatment agent to prevent adhesion of bacteria to matrix proteins exposed in wound tissue and for prophylactic use in dental treatment as an alternative to or in conjunction with, antibiotic prophylaxis. Alternatively, the composition of the invention may be used to bathe an indwelling device immediately before insertion. The active agent will preferably be present at a concentration of 1 μg/ml to 10 mg/ml for bathing of wounds or indwelling devices.

A vaccine composition is conveniently in injectable form. Conventional adjuvants may be employed to enhance the immune response. A suitable unit dose for vaccination is 0.5–5 microgram/kg of antigen, and such dose is preferably administered 1–3 times and with an interval of 1–3 weeks. With the indicated dose range, no adverse toxicological effects will be observed with the compounds of the invention which would preclude their administration to suitable individuals.

Each reference disclosed herein is incorporated by reference herein in its entirety. Any patent application to which this application claims priority is also incorporated by reference herein in its entirety.

EXAMPLES

The present invention is further described by the following examples. The examples are provided solely to illustrate the invention by reference to specific embodiments. These exemplifications, while illustrating certain specific aspects of the invention, do not portray the limitations or circumscribe the scope of the disclosed invention.

All examples were carried out using standard techniques, which are well known and routine to those of skill in the art, except where otherwise described in detail. Routine molecular biology techniques of the following examples can be carried out as described in standard laboratory manuals, such as Sambrook et al., *MOLECULAR CLONING: A LABORATORY MANUAL*, 2nd Ed.; Cold Spring Harbor Laboratory Press, Cold Spring Harbor, N.Y. (1989).

All parts or amounts set out in the following examples are by weight, unless otherwise specified.

Unless otherwise stated size separation of fragments in the examples below was carried out using standard techniques of agarose and polyacrylamide gel electrophoresis ("PAGE") in Sambrook et al., *MOLECULAR CLONING: A LABORATORY MANUAL*, 2nd Ed., Cold Spring Harbor Laboratory Press, Cold Spring Harbor, N.Y. (1989) and numerous other references such as, for instance, by Goeddel et al., *Nucleic Acids Res.* 8: 4057 (1980).

Example 1

PCR With Random Primers

This method describes a rapid way to obtain additional sequence data from partial gene fragments independent of probing a genomic library.

Random sequencing of a *S. aureus* genomic library followed by sequence homology searching with the *B. subtilis* P-protein sequence resulted in the identification of a 324 base pair (herein "bp") fragment. The first 193 nucleotides of this fragment showed significant homology to the C-terminal half of the *B. subtilis* P-protein and other prokaryotic RNase P proteins. The N-terminal domain of the putative *S. aureus* RNase P protein was putatively missing.

A novel two step PCR with two different reverse primers complementary to the known sequence in position 15–39 and 194–215 respectively (shown below, Table 2) as well as random hexamer primers (Gibco) was used to obtain the complete 5' sequence of the *S. aureus* spp gene. *S. aureus* genomic DNA partially digested with Hind III or Pst I served as a template. Primer #1 (position 194–215) annealed just downstream of the stop codon TAA and primer #2 (position 15–39) close to the end of the known sequen, e (see Table 2).

TABLE 2

Primer Position

5' GAATT CCGTG TTAAG AAACA AGATT AAAAG AGCAA TACGT GAAAA TTTCA AAGTA CATAA GTCGN

3'C TTTGT TCTAA TTTTC TCGTT ATGC 5' [SEQ ID NO:7]

ATATA TTGGN CAAAG ATATT ATTGN TATAG NAAGA CAGGC AGCTA AAGAT ATGAC GACTT TACAA

ATACA GNATA GTCTT GAGCA CGTNC TTAAA ATTGG CAAAG TTTTT AATAA AAAGA TTAAG TAAGG

TABLE 2-continued

Primer Position

3'CC

ATAGG GTAGG GAATG AAAAC ATTAA CCCCT CAACG CATCC CGAAG TCTTA CCTCA GACAA

ACGTT

*TATCC CATCC CTTAC TTTTG* 5' [SEQ ID NO:8]

AGACT GACCC TAGGG TTAAG ACTTG GCCCN AGGGN TATNN TAACT TACTT TAAAA TGTTT

TCAC 3' [SEQ ID NO:4]

In the first step, the reverse strand encoding the C-terminus and upstream the unknown N-terminal sequence of the protein was amplified using primer #1, resulting in single stranded products. This amplification of the desired sequence favoured the binding of random primers to that sequence in the next step.

In the second step, $^{32}$P-end-labeled primer #2 and random hexamers were added and the annealing temperature was dropped to 25° C. to allow the short random primers to anneal to the DNA.

The PCR is expected to generate many different fragments, however the major products should be those primed by primer #2 and a random primer (see below). Only these products were of interest as they should encode the N-terminal half of the protein and they could be monitored since they would be radiolabeled. After separation of the PCR products by gel electrophoresis and exposure to film, a limited number of radiolabeled bands should be visible on the autoradiogram. These fragments can subsequently be cloned into a suitable vector, e.g., pUC19, and sequenced using routine methods.

Example 2

PCR of the spp 5' Domain With Random Primers

The 5' half of the spp gene was amplified in a two step PCR reaction as described herein. The PCR products were cleaned using a QIAquick PCR purification column and recovered in 50 µl water. The sample was concentrated to a final volume of 25 µl under vacuum in a SpeedVac® SC110 (Savant). 20 µl were loaded onto a 1.6 mm, 8% polyacrylamide gel containing 7M urea and analyzed by gel electrophoresis. The gel was stained with ethidium bromide (1 µg/ml in $H_2O$) to visualize the DNA and photographed. The gel was then dried and exposed to film.

There were several defined bands visible both on the ethidium bromide stained gel as well as on the autoradiogram. They ranged in size between 50 bp to over 2000 bp, some bands being more intense than others. The most prominent bands were approximately 50 bp, 150 bp, 400 bp and 800 bp in size.

Example 3

Shotgun Cloning of the PCR Fragments: Cloning and Sequencing of the PCR Fragments The PCR fragments were blunt end cloned into SmaI cut pUC19. Ligations of 100 ng vector DNA with 1.0 µl and 1.5 µl of PCR products were performed at 16° C. overnight. *E. coli* XL1 blue cells (α-complementing) were transformed by electroporation and plated onto selective plates containing IPTG and x-gal (for blue/white screening). Transformation of these cells resulted in approximately 8.5% white colonies in the presence of PCR products, whereas only 4.6% white colonies could be found in the control ligation without insert. White colonies had lost the ability to form the β-galactosidase holoenzyme as a result of a reading frame disruption in the lacZ' gene and were no longer able to cleave x-gal. The reading frame was either disrupted by an insert (in the presence of PCR products) or exonuclease activity of the restriction enzyme preparation, destroying the Sma I site of the vector by cleaving terminal nucleotides and resulting in frame shifts after ligation.

18 white colonies were picked and grown up as 2 ml cultures to prepare plasmids. A sample of each plasmid was linearized with AccI restriction endonuclease (cuts in the multi cloning site) and run on a 1% TAE agarose gel alongside the original pUC19.

The results showed that 7 plasmids released a short fragment upon restriction digest. As there is only one AccI site in pUC19, these recombinant plasmids must contain an insert with a restriction site for this enzyme. 3 plasmids appeared larger than pUC19 but did not release a fragment. The other 8 plasmids were of the same size as pUC19 and did not appear to have an insert.

The 10 plasmids containing an insert were sequenced both with the forward and reverse pUC/M13 sequencing primers.

5 of the 6 plasmids that released a fragment after AccI digest harboured an 213 bp insert that started with the primer #2 sequence and the known 14 bp followed by a sequence of 174 nucleotides that was common to all of the plasmids (Sequence 1, Table 3). In one of the 6 plasmids the insert (Sequence 2, Table 3) was slightly different: the first 137 nucleotides were in common with Sequence 1 (dotted line), however the insert sequence extended beyond this and deviated from Sequence 1 (see Table 3):

TABLE 3

Aplification Product Sequence 1, 2 and 3

Sequence 1 [SEQ ID NO: 9]
5'GTTTT CATTC CCTAC CCTAT CCTTA CTTAA TCTTT TTATT AAAAA

GAATG CAGAT TTTCA GAGAA TATAT AAAAA AGGTC ATTCT GTAGC

CAACA GACAA TTTGT TGTAT ACACT TGTAA TAATA AAGAA ATAGA

CCATT TTCGC TTAGG TATTA CTGTT TCTAA AAAAC TAGG*T* AAT*GC*

<u>AGTGTTAA*GA* ACAAG ATTAA AAGAG CAATA CGT</u> 3'

Sequence 2 [SEQ ID NO: 10]
5'.....ACGAT AAATA ACAGT ATGTT ATTGG AAAAA GTCTA CCGAA TTAAA

AAGAA TGCAG ATTTT CAGAG AATAT ATAAA AAAGG TCATT CTGTA GCCAA

CAGAC AATTT GTTGT ATACA CTTGT AATAA TAAAG AAATA GACCA TTTTC

GCTTA GGTAT TAGTG TTTCT AAAAA ACTAG G*T*AAT *G*CAGT GTTAA GAACA

AGATT AAAAG AGCAA TACGT 3'

Sequence 3 [SEQ ID NO: 11]
5'... GAAAA TTTCA AAGTA CATAA GTCGC ATATA TTGGC CAAAG ATTGT

AATAG CAAGA CAGCC AGCTA AAGAT ATGAC GACTT TACAA ATACA GAATA

GTCTT GAGCA CGTAC TTAAA ATTGC CAAAG TTTTT AATAA AAAGA TTAAG

TAAGG ATAGG GTAGG GAATG AAAAC 3' stop codon (underlined)

Primer #2 sequence is shown in bold and also the known 14 bases underlined (3 changes to known sequence in italic).

The predicted translation products showed significant homology to B. subtilis P-protein and indicated that these inserts contain the full sequence information for the 5' domain of the spp gene.

In 2 plasmids the insert started with the sequence of primer #1 followed by 3' half of the spp gene (Sequence 3, Table 3). This sequence was already known but the new sequence showed 9 base changes (shown in bold) in comparison to the original sequence data obtained by random sequencing of the S. aureus library.

2 plasmids contained inserts with different sequences that are a result of unspecific priming during PCR.

Example 4

Analysis of the Sequence Data

The newly obtained sequence data was drawn together and predicted to represent the complete sequence of the spp structural gene. The reading frame was determined from a partial sequence of the 3' domain. According to this reading frame the start codon ATG could be identified 174 bp upstream of primer #2 sequence (see above). The total length of the gene is 354 bp.

The nucleotide sequence of the spp gene is shown in Table 1 [SEQ ID NO:2]; the start codon (ATG) and stop codon (TAA) are both shown in bold. The deduced translation product of the spp gene (SP protein) is 117 amino acids is also shown in Table 1 [SEQ ID NO:2].

The translated sequence was aligned with known amino acid sequences of the RNase P protein from 5 different prokaryotes. The S. aureus SP protein sequence matched the B. subtilis P-protein sequence well, significant homology to the B. subtilis protein.

Example 5

PCR of the spp Gene

The newly obtained sequence data was used to design PCR primers for the amplification of the full length spp structural gene.

The PCR resulted in a single band of approximately 360 bp with a total DNA yield of 2 µg as determined by spectrophotometrical measurement. The DNA fragment was cleaned using a QIAquick PCR purification column and recovered in 80 µl water.

Example 6

Cloning spp Into pMalc2

The pMalc2 vector provides a method for expressing and purifying a protein produced from a cloned gene (New England BioLabs) (see also, Guan, C., Li, P., Riggs, P. D. and Inouye, H. (1987) Gene 67, 21–30; Maina, C.V. et al. (1988) Gene 74, 365–373: Riggs, P. in Ausubel, F.M. et al.

(eds) Current prot. in Molecular Biol. (1992): Kellerman and Ferenci (1982) Methods in Enzymol. 90, 459–463; Yanisch-Perron, C. et al (1985) Gene 33, 103–119; Zagursky, R. J. and Berman, M. L. (1984) Gene 27, 183–191, regarding the vector and its uses).

The cloned gene is inserted downstream from the malE gene of E. coli, which encodes the maltose-binding-protein (MBP), resulting in the expression of an MBP fusion protein. The method uses the strong "tac" promotor under the control of the lac repressor and a one step purification of the fusion protein using MBP's affinity for maltose. Unique restriction sites are available between malE and lacZa for inserting the gene of interest, allowing blue/white screening of transformants. The vector also contains a recognition site for the specific Factor Xa protease located just 5' to the polylinker. This allows MBP to be cleaved after purification without leaving any vector derived residues attached to the protein of interest when the gene is cloned into the Xmnl site.

Example 7

Ligation of the spp PCR Product Into pMalc2

1 μg of the protein fusion vector pMalc2 was cut with XmnI and BamHI restriction endonucleases to enable directional cloning of the spp structural gene. To remove the small 15 bp insert the digest was cleaned using QIAquick PCR purification column and the DNA recovered in 90 μl water. A sample was analysed by agarose gel electrophoresis to ensure complete digestion of the vector. After 30 min of incubation at 37° C. with both enzymes the vector was completely cut.

The spp PCR product was digested with BamHI and cleaned using a QIAquick PCR purification column.

Vector and insert were ligated overnight in a 20 μl reaction at 16° C. The molar ratio of vector to insert was 1:5. To prepare the DNA for electroporation, the ligation was desalted using QIAquick Nucleotide Removal columns.

Example 8

Transformation of E. coli XL-1 Blue Cells

40 μl electrocompetent E. coli XL-1 Blue cells were transformed with 2 μl desalted ligation reaction. Cells were recovered in 1 ml SOC medium after electroporation. 50 μl of a 1:100 dilution were plated onto an LB plate containing ampicillin, IPTG and x-gal and incubated at 37° C. overnight. 11 white and 1 blue colony were recovered. The 11 white colonies were grown up and the plasmids were isolated from the clones. Sequencing of the plasmids showed that 6 of the 11 plasmids contained the correct spp insert. The resulting plasmid was denoted pMalc2::spp, and the fusion protein product MBP-SPP.

Example 9

Growth of Cells and Fusion Protein Induction in E. coli XL-1 Blue pMalc2::spp

A 1 liter culture of E. coli XL-1 Blue pMalc2::spp was grown at 37° C., 220 rpm and expression of the MBP-SPP fusion induced by adding ImM IPTG at an $A^{600}$ of 0.6. Induction was continued for 2 hours. The $A^{600}$ was monitored over that time period to ensure that cells were still growing during induction. Iml samples were removed from the culture after 0.5, 1.0 1.5 and 2 hours, the cells pelleted and the pellet resuspended in 100 ll SDS gel loading buffer.

3 μl of the samples were analysed by SDS-PAGE with Coomassie staining.

The cells were not effected by the overexpression of the fusion protein, they kept growing and after 2 hours of IPTG induction reached an $A^{600}$ of 1.43.

Protein extracts from samples were separated by SDS-PAGE and transferred onto a nitro-cellulose membrane by Western transfer. The MBP-SPP fusion protein could be immuno-detected by incubation of the membrane with anti-MBP rabbit serum and HRP-coupled anti-rabbit antibodies followed by ECL detection. The Western Blot revealed that 2 proteins were induced upon IPTG addition. The major protein was of the expected size of approximately 56kD, the second protein, produced in lower amounts, was 10–15 kD larger. Analysis of the spp sequence revealed an accumulation of AUA (ile) and AGA (arg) codons that are rare in E. coli. The normal frequency of AGA in E. coli is 0.27%, of AUA 0.51%. The spp sequence consists to 4.3% of AGA and 5.1% of AUA. These codons may cause frame shifts and other altered translation events when overexpressing a protein with a high abundance of rare codons.

Another E. coli strain was available that constituively expresses the ArgU tRNA ($tRNA^{UCU}$) and IleX tRNA ($tRNA^{UAU}$) from the plasmid pRI952.

Example 10

Transformation of E. coli W3110 pRI952

50 μl electrocompetent E. coli W31 10 pRI952 cells were transformed with 2 μl desalted ligation reaction. Cells were recovered in Iml SOC medium after electroporation. 100 μl of the culture were plated onto selective LB plates (ampillin, cam) containing IPTG and x-gal and incubated at 37° C. overnight. Too many colonies grew on the plate and could not be counted. 5 white colonies were selected and their plasmids isolated. Sequencing of the plasmids showed that all contained the correct spp insert.

Example 11

Growth of Cells and Fusion Protein Induction in E. coli W3110 pRI952 pMalc2::spp The cells were grown and the expression of the fusion protein was induced as described above. The cells kept growing during the induction period from an $A^{600}$ of 0.6 to 1.45. Samples were taken from the culture at 0.0, 0.5, 1.5 and 2.5 hours after IPTG addition and protein extracts analysed by SDS-PAGE with Coomassie staining, as well as Western transfer with immunodection. Overexpression of the rare tRNAs IleX and ArgU resulted in only one MBP-SPP fusion protein being overexpressed during IPTG induction as detected by the anti-MBP serum.

Example 12

Purification of the MBP-SPP Fusion by Affinity Chromatography

Following optimal induction, the cells (E. coli W3110 pRI952 pMalc2::vpp) were harvested and disrupted by sonication after a freeze-thaw cycle to weaken the cell wall using known methods. The cell debris was removed by centrifugation and the protein concentration of the crude extract determined using the BIO-RAD Protein Assay. The total amount of protein in the crude extract was 86 mg. A sample of the crude extract was analysed by SDS-PAGE with Coomassie staining which showed that the fusion protein was released from the cells during sonication.

The crude extract was then pumped through the amylose resin column, to which the MBP-SPP fusion bound, and unbound protein was removed from the column by extensive washing with column buffer. The fusion protein was then eluted with column buffer supplemented with 10mM maltose using methods described herein. The eluate was collected as 3 ml fractions. Samples were removed during the purification procedure and analyzed by SDS-PAGE with Coomassie staining. Almost all of the fusion protein bound to the amylose resin, only trace amounts were found in the flow-through and no fusion protein was washed off the column. Fractions 4–11 contained reasonable amounts of protein and were pooled, yielding in 25 ml protein solution with a concentration of 1 mg/ml.

Example 13

Factor Xa Cleavage of the Fusion Protein and Separation of MBP and SPP

500 μg Factor Xa protease were added to the solution and the fusion protein was cleaved overnight at 4° C. A sample was analysed by SDS-PAGE before and after Factor Xa incubation to monitor complete cleavage. After 15 hours almost all the fusion protein was cleaved resulting in the 42 kD MBP and SPP of approximately 14kD.

The SP protein readily precipitated upon Factor Xa cleavage and could be separated from MBP by centrifugation. The SPP pellet was washed 3 times and then resuspended in 5ml column buffer. The MBP remained in solution and was found in the supernatant whereas the pellet consisted mainly of the SP protein and one minor contaminating protein, resulting in a reasonably pure preparation of SPP. The total SPP yield was 2.18 mg/liter culture. The SPP preparation was diluted with column buffer to a final concentration of 0.32 mg/ml. 1 mM DTT was added to prevent intermolecular disulfide bond formation between cystein residues. The addition of 7M urea denatured and apparently completely resolubilized the protein. The protein was aliquoted, snap-frozen and stored at –80° C.

Example 14

In vitro Transcription of the SP RNA

SP RNA was transcribed in vitro from the plasmid pSPR using T7 RNA polymerase. pSPR is a pUC19 derivative that harbours the *S. aureus* spr gene behind a T7 promotor. The plasmid was linearized with BamHI restriction endonuclease to enable run off transcription. The Ambi on MEGAscript™ T7 kit was used for large scale transcription of the SP RNA. The transcription reaction was performed at 30° C. to allow slow folding of the RNA into the correct conformation during synthesis. The RNA was cleaned under non-denaturing conditions using CLONTECH Chroma-Spin 30 columns and the RNA recoverd in 40 μl water. The quality of the transcript was monitored by gel electrophoresis on a 5% polyacrylamide TBE gel with 7M urea. The RNA was visualized by UV-shadowing over a TLC plate.

In vitro transcription of SP RNA from pSPR resulted in a single RNA product of the expected size of 401 nucleotides. The total RNA yield was 140 μl (determined spectrophotometrically). After cleaning, the RNA was recovered in 40 μl water resulting in a 29 μM solution, that was stored at –20° C.

Example 15

In vitro Transcription of *E. coli* ptRNA$^{met}$ Incorporating [α-$^{32}$P] UTP

*E. coli* ptRNA$^{met}$, a substrate for RNase P, was transcribed in vitro by T7 RNA polymerase (Epicenter) in the presence of [α-32P] UTP to internally label the RNA. The DNA template pGem3Z-ptRNA was linearized with BstNI restriction endonuclease to allow run-off transcription. The transcription was performed in a 20 μl reaction at 37° C. for 60min. To remove unincorporated nucleotides the 93 nt RNA (sequence shown below) was cleaned under non-denaturing conditions using a CLONTECH Chroma-Spin 10 column. To calculate the specific activity of the RNA probe, 1 μl samples were removed before and after cleaning, mixed with 5 ml scintillation cocktail and counted in a scintillation counter. ptRNAmet in pGem-3Z, sequence of the transcript (93mer) 5'→3' [SEQ ID NO: 12]: GGGCG AAUUC GCCUC GGCUA CGUAG CUCAG UUGGU UAGAG CACAU CACUC AUAAU GAUGG GGUCA CAGGU UCGAA UCCCG UCGUA GCCAC CAG Transcription of ptRNA$^{met}$ resulted in a 2 μM (6 ng/μl) solution. 64.3% of the nucleotides were incorporated in the transcript and the specific activity was $2.1710^x$ cpm/μg.

Example 16

5' End-labeling of p6AT-1

The chemically synthesized 42nt RNA molecule p6AT-1 was 5' end-labeled with high specific activity [γ-$^{32}$p] ATP (6000 μCi/μl) using bacteriophage T4 polynucleotide kinase. The labeling was performed in a 10 μl reaction at 37° C. for 30 min. The enzyme was heat-inactivated at 95° C. for 2 min. To remove salts, unincorporated nucleotides and the enzyme, p6AT-1 was gel purified from a 20% polyacrylamide TBE gel with 7M urea. The RNA was extracted from the gel slice and precipitated with 300 mM NaOAc and 2.5 volumes 100% ethanol. After a spin at 14,000 g and 4° C. the RNA pellet was washed twice with chilled 70% ethanol. The pellet was air dried and subsequently resuspended in 50 μl water. 0.5 μl were spotted onto a filter paper disk and counted in a scintillation counter (Cherenkov analysis).

The end-labeling resulted in a p6AT-1 preparation with an activity of 640,000 cpm/μl.

Example 17

Determination of the Optimal Buffer Conditions for SP RNA Reactions

*E. coli* M1 RNA is able to cleave ptRNA$^{met}$ or the minimal substrate p6AT-1 in 100 mM NH4Cl, 100 mM TrisCl pH 7.5, 100 mM MgCl$_2$. The conditions for cleavage of either substrate by *S. aureus* SP RNA were unknown and clearly deviated from those optimized for *E. coli*. A large number of different buffer conditions were investigated in order to determine optimal buffer conditions for either substrate cleavage by the *S. aureus* ribozyme.

Cleavage reactions (20 μl) were all performed at 37° C. for 30 min with 100 nM SP RNA and an additional 200 nM SP protein in the holoenzyme reactions. Substrates (ptRNA$^{met}$ or p6AT-1) were added in trace amounts (single-turnover reactions). Cleavage was monitored by size resolution of the intact precursor and the cleaved leader sequence by denaturing gel elctrophoresis and autoradiography or visualization on the phosphorimager (Molecular Dynamics Storm 860).

Example 18

Effect of KCl Versus NH$_4$Cl on p6AT-1 Cleavage

All experiments were performed in 100 mM TrisCl pH7.5, 100 mM MgCl2 and 1M or 2M monovalent salt (KCl or NH4Cl). There was hardly any cleavage product detectable at 1M KCl or NH4Cl. Cleavage occurred when 2M monovalent salt were used. Potassium chloride gave better results than ammonium chloride.

Further optimization of the monovalent salt concentration was investigated following optimization of additional parameters described in the following sections.

Example 19

Effect of the pH on p6AT-1 Cleavage

Buffers containing 100 mM MgCl2, 2M KCl and 100 mM Tris Cl at a pH of 7.0, 7.5 and 8.0 were tested for the ability to promote p6AT-1 cleavage by SP RNA. The substrate was cleaved in all three buffers but cleavage was very poor at pH 7.0 and optimal at pH 8.0.

Example 20

Influence of PEG 8,000 on p6AT-1 Cleavage

The addition of polyethylene glycol has been shown to improve substrate cleavage by E. coli M1 RNA. Here the effect of different PEG 8,000 concentrations on p6AT-1 cleavage by SP RNA was demonstrated. 1%, 2.5% and 5% PEG were added to reactions containing 1M KCl, 100 mM TrisCl pH8, 100 mM MgCl2. The ability to cleave the substrate improved with increasing PEG concentrations, and therefore 5% PEG was selected to be included in subsequent reactions.

Example 21

$MgCl_2$ Requirements for p6AT-1 Processing

The MgCl2 concentration was successively reduced from 100 mM to 10 mM to determine the lowest magnesium ion concentration at which the SP RNA could still process the substrate. 100 mM, 50 mM, 25 mM and 10 mM MgCl2 were tested in a buffer containing 2M KCl, 100 mM TrisCl pH8 and 5% PEG.

Cleavage results were obtained at 100 mM MgCl2. However SP RNA was still able to process p6AT-1 at 50 mM and to some extend at 25 mM MgCl2. No cleavage could be observed at 10 mM MgCl2.

Example 22

Determination of KCl Requirements for p6AT-1 Cleavage

The KCl concentration was successively increased from 40 mM to 1.5M in 100 mM TrisCl pH8, 100 mM MgCl2 and 5% PEG.

No cleavage occurred at KCl concentrations below 400 mM. At 400 mM KCl p6AT-1 processing was still very poor but increased with the salt concentration to reach a maximal level of 27% at 1.5M KCl. That was comparable to p6AT-1 cleavage by E. coli M1 RNA, where 35% of the substrate was cleaved after 20 min. The best buffer conditions for p6AT-1 cleage by SP RNA were 1.5M KCl, 100 mM TrisCl pH8, 100 mM MgCl2, 5% PEG.

Example 23

KCl Requirements for ptRNA$^{met}$ Cleavage by SP RNA ptRNA$^{met}$ was cleaved under the same buffer conditions as described above. ptRNA$^{met}$ was a better substrate than p6AT-1. By contrast to p6AT-1, ptRNAmet could be processed at KCl concentrations below 400 mM. Some cleavage could already be detected at 20 mM KCl, whereas no cleavage of p6AT-1 was observed under these conditions. The cleavage rate increased with the KCl concentration. At 150 mM KCl more than 50% of the substrate was processed, reaching 82% at 800 mM KCl. At concentrations of 1M or above 85% of the ptRNA were cleaved, and no further increase could be detected, indicating that 15% of the substrate was uncleavable. E. coli M1 RNA as a positive control cleaved 80% of the substrate in 100 mM Tris.Cl pH7.5, 100 mM NH4Cl, 100 mM MgCl2 within 20 min. The best buffer conditions for ptRNA$^{met}$ cleavage by SP RNA were 1M KCl, 100 mM TrisCl pH8, 100 mM MgCl2, 5% PEG.

Example 24

Determination of the Optimal Buffer Conditions for S. aureus RNase P Holoenzyme Reactions: p6AT-1 Cleavage by the Holoenzyme The S. aureus RNase P holoenzyme cleavage of p6AT-1 was investigated over a range of different KCl concentrations at low magnesium ion concentrations. All reactions were performed in 100 mM TrisCl pH8, 10 mM MgCl2, 5% PEG and 40 mM to 1.5M KCl. Cleavage could already be observed at 40 mM KCl. The cleavage rate increased with the concentration of monovalent salt, peaking at 150 mM, where 50% of the substrate was processed. At higher KCl concentrations the cleavage rate decreased again and p6AT-1 processing did not occur at KCl concentrations of 600 mM and above. The E. coli holoenzyme control cleaved 57% of the p6AT-1 within 20 min in 100 mM Tris.Cl pH7.5, 100 mM NH4Cl, 10 mM MgCl2. The optimal buffer for p6AT-1 cleavage by the holoenzyme was 150 mM KCl, 100 mM Tris.Cl pH 8.0, 10 mM $MgCl_2$, 5% PEG 8000. p6AT-1 was a better substrate for the holoenzyme than for SP RNA, as under optimal conditions only 27% p6AT-1 was cleaved as opposed to 50% by the S. aureus RNase P holoenzyme.

Example 25

$MgCl_2$ Requirements for ptRNA Cleavage by the Holoenzyme

The S. aureus RNase P holoenzyme failed to cleave ptRNA$^{met}$ under the same conditions employed for p6AT-1 processing. The holoenzyme was not able to cleave the substrate at 10 mM $MgCl_2$ under any given KCl concentration. The concentration of magnesium ions was increased to 20 mM and ptRNA cleavage by the holoenzyme as well as the SP RNA ribozyme were tested at different KCl concentrations. The buffers contained 100 mM TrisCl pH8, 20 mM $MgCl_2$, 5% PEG and 10 mM, 50 mM, 150 mM, 600 mM or 1.5M KCl.

Cleavage of ptRNA by the holoenzyme at 10 mM $MgCl_2$ and low KCl concentrations was very poor. At 20 mM MgCl2 and 150 mM KCl the holoenzyme processed ptRNA very well, 54% of the substrate was cleaved within a 20 min incubation. Only a low percentage of substrate processing could be detected at 600 mM KCl, but good cleavage occurred at 1.5M KCl. The SP RNA alone was also able to cleave ptRNA under these conditions but was unable to cleave ptRNA at lower salt concentrations. Therefore the optimal $MgCl_2$ concentration for ptRNAmet cleavage by the holoenzyme was 20 mM.

Example 26

Determination of the Optimal KCl Concentration

The S. aureus RNase P holoenzyme was tested for its ability to cleave ptRNA$^{met}$ under different KCl concentrations ranging from 20 mM to 1.5M. The buffers contained 100 mM TrisCl pH8, 20 mM MgCl$_2$, 5% PEG 8000 and xM KCl.

The holoenzyme was able to cleave ptRNAmet at KCl concentrations as low as 20 mM. The cleavage rate increased with the salt concentration with a peak at 150 mM where 55% of the substrate was processed. The cleavage rate decreased at KCl concentrations above 200 mM but improved again at 1M KCl reaching a maximum at 1.5M. The cleavage at high salt concentrations was not due to holoenzyme activity but result of SP RNA ribozyme activity at high KCl concentrations.

ptRNA$^{met}$ was a better substrate for SP RNA than for the S. aureus RNase P holoenzyme. The optimal buffer conditions for ptRNAmet cleavage by the holoenzyme were 150 mM KCl, 100 mM TrisCl pH8, 20 mM MgCl$_2$, 5% PEG.

Example 26

Strain Selection, Library Production and Sequencing

The polynucleotide having the DNA sequence given in SEQ ID NO:1 was obtained from a library of clones of chromosomal DNA of Staphylococciis autreus in E. coli. The sequencing data from two or more clones containing overlapping Staphylococcus aureus DNAs was used to construct the contiguous DNA sequence in SEQ ID NO:1. Libraries may be prepared by routine methods, for example: Methods 1 and 2 below.

Total cellular DNA is isolated from Staphylococcus aureus WCUH 29 according to standard procedures and size-fractionated by either of two methods.
Method 1

Total cellular DNA is mechanically sheared by passage through a needle in order to size-fractionate according to standard procedures. DNA fragments of up to 11 kbp in size are rendered blunt by treatment with exonuclease and DNA polymerase, and EcoRI linkers added. Fragments are ligated into the vector Lambda ZapII that has been cut with EcoRI, the library packaged by standard procedures and E. coli infected with the packaged library. The library is amplified by standard procedures.
Method 2

Total cellular DNA is partially hydrolyzed with a one or a combination of restriction enzymes appropriate to generate a series of fragments for cloning into library vectors (e.g., RsaI, PalI, AluI, Bshl235I), and such fragments are size-fractionated according to standard procedures. EcoRI linkers are ligated to the DNA and the fragments then ligated into the vector Lambda ZapII that have been cut with EcoRI, the library packaged by standard procedures, and E. coli infected with the packaged library. The library

Example 27

Structure Probing

S. aureus RNase P RNA was in vitro transcribed by T7 RNA polymerase and its structure was probed with a variety of enzymatic and chemical probes. Probing data indicates that the S. aureus RNase P RNA adopts a similar, but unique secondary structure to that of B. subtilis RNase P RNA. Filter binding and gel-shift assays showed that S. aureus RNase P protein binds to the RNA specifically. The binding constant of the complex was measured to be 20 nM. The S. aureus holoenzyme, as well as the RNA component alone, have been shown to be functional and the holoenzyme demonstrated a K$_m$ of 53±4 nM and a k$_{cat}$ of 3.4±0.1 min$^{-1}$ with cloned S. aureus pre-tRNA$^{phe}$ as substrate under the experimental conditions. (1) Frank, D. N. an Pace, N. R. Ann. Review Biochem. (1998), 67, p.153–80. (2) Massire, C., Jaeger L., and Westhof, E. J. Mol. Biol. (1998), 279, p. 773–93.

A partial homology to the B. subtilis RNase P RNA sequence was identified from a randomly sequenced S. aureus genornic library. The complete structural gene encoding the RNase P RNA was amplified and cloned by a 3' primer of known sequence and a 5' degenerate primer designed to form the conserved P1 helix. The 5'-end sequence of the RNA was confirmed by primer extension using endogenous S. aureus RNA. S. aureus protein gene, spp, was identified in a similar manner. The gene was amplified, cloned, and expressed in E. coli as a maltose binding fusion. The MBP tag was cleaved off by Factor Xa and the native protein was purified by column chromatography. The RNA secondary structure and potential tertiary interactions were studied by enzymatic and chemical probing. The enzymatic probes included RNase T1, U2, V1, and T2. Chemical probes included DEPC. The RNase P RNA/protein interactions were investigated by gel mobility shift and filter binding experiments. A cloned pre-tRNA$^{phe}$ was used as a substrate for kinetic characterizations for both the holoenzyme and RNA only reactions. The endogenous RNA used in primer extension experiments was isolated from S. aureus cells by TRIZOL method.

S. aureus RNase P Gene Sequence

The entire gene sequence (398nts) was recovered by a 3' primer of known sequence and a 5' degenerate primer designed to form the P1helix. The 5'-end sequence was confirmed by primer extension usingendogenous S. aureus WCUH29 RNA. The 5' most G could not be distinguished by pnrmer extension experiments, however, this nucleotide (nt) is contained in the clone we used to transcribe RNase P RNA which has been shown to be functional.

Michaelis Menten Plot of RNase P holoenzyme kinetics was determined under the following conditions: 1×buffer: 100 mM Tris-Cl, pH7.0, 150 mM KCl, 10 mM MgCl2, 5% PEG, [E]=20 nM. Results from at least two independent experiments for holoenzyme: K$_m$=53±4 nM and k$_{cat}$=3.4±0.1 min$^{-1}$. RNase P RNA-only kinetics in the following buffer: 50 mM Tris, pH8.0, 1 M NH$_4$Cl, 200 mM MgCl$_2$, and 5% PEG. Pre-tRNA$^{phe}$ is efficiently processed by the ribozyme. In both experiments, a cloned pre-tRNA$^{phe}$ was used as substrate.

Binding isotherm of RNase P RNA obtained by filter binding assay was asswssed. The 3'-end labeled RNA was mixed with the protein in the binding buffer containing 20 mM K-Hepes, pH8.0, 0.01% NP-40, 400 mM NH$_4$OAc, 10 mM MgCl$_2$, and 5% glycererol. The K$_d$ value was generated by fitting the data with Grafit 4 one-site ligand binding equation: % binding=plateau/(1+K$_d$/[S. aureus protein]). K$_d$=8±1 nM from at least three independent experiments.

Structural probing of 5'-end labeled S. aureus RNase P RNA reveled probing data demonsrating that RNase V1 cleavage occurred at 8–11; 16–23; 30–33; 37–54; 64–84; 96–105; 119–130; 150–156; 166–169; 181–184; RNase T2 cleavage: 24–27;55–60; 86–91; 106–108; 135–138; 170–177 (but was weak) Nucleotides (also "Nts" or "nts") 139–149 (P10.1a(3') and the internal loop) and P12(3') are not accessible to both enzymes, indicating that these nts may be buried in the structure. Nucleotides 166–169 (J11/12) were sensitive to RNase V1 cleavage, indicative of helical nature of the sctructure.

Structural probing of 5'-end labeled *S. aureus* RNase P RNA using DEPC revealed cleavage data that agrees well with enzymatic data providede herein. Strong cleavage was observed mainly in loops, e.g. nts 159–161, A211–213.A203, 204, and A169 only showed mild reactivity indicating possible tertiary interactions. These data suggest that A130 may basepair with U141, and U129 basepairs with A142, with A131 as one nt bulge.

Structural probing of 5'-end labeled *S. aureus* RNase P RNA revealed strong cleavage observed mainly in loops, e.g. L5.1 and L8. Moderate cleavage of A69 suggested that J5.1/7 is single-stranded. A106 and A107 only exhibited mild cleavage indicating a possible tertiary interaction. The strong cleavage of A59 does not support a tertiary interaction of this nt which is proposed for this nt with nt in L15.1 in *B. subtilis* structure.

Structural probing of 3'-end labeled RNA using DEPC showed strong DEPC cleavage at 292–294 (L15.2), and 271(bulged A). No obvious cleavage in A266 and A267 (L15.1) was observed indicative of tertiary interactions. Nts 281–286 (P15.2(5')) showed RNase V1 activity, whereas nts 290–294 (L1 5.2) were sensitive to RNase T2.

Structural probing of 3'-end labeled *S. aureus* RNase P RNA using nucleases V1 and T2 revealed data that strongly indicates the existence of helix P15.2 and unstructured L15.2. DEPC data is consistent with V1 and T2. DEPC Strong cleavage occurred in loop L15.1, L15.2 and a bulged A271. Mild cleavage was seen in part of J15.2/2. Minor cleavage of A266 and A267 indicates that these two nts may be involved in tertiary interactions. A332 in L19 is likely to be paired with U349 as both A332 and C331 were sensitive to RNase V1.

Structural probing results demonstaretd that the conserved regions of *S. aureus* RNase P RNA adopt similar, though unique structural properties to its *E. coli* and *B. subtilis* counterparts. Moreover, the conserved regions P1, P4, P12, P15, P15.1, and P15.2 have been confirmed by RNase V1 cleavage. Strong DEPC cleavage was observed in L8, J10.1/11, L15, L15.1, and L15.2, which further supports the structural model. Strong DEPC cleavage of L15.2 was observed indicating this region is not structured. V1 cleavage data supports evidence for P4 long range interaction. Evidence supports possible internal loop interaction in L19. P12(3') and J12/11 are mainly not accessible to the enzymes but mildly accessible to smaller chemical probes such as DEPC. This phenomenon was further observed by primer extension experiments, indicating this region is most likely involved in tertiary interactions. Part of J11/12 was sensitive to RNase V1 cleavage indicative of possible helical nature.

What is claimed is:

1. An antagonist that inhibits or an agonist that activates an activity of an RNA selected from the group consisting of: an RNA transcribed from a polynucleotide comprising an nucleotide sequence having at least a 90% identity to the amino acid sequence of SEQ ID NO:3, and an RNA transcribed from a polynucleotide comprising an nucleotide sequence set forth in SEQ ID NO:3, wherein said activity is selected from the group consisting of:

*Staphylococcus aureus* RNaseP $K_m$=53±4 nM determined in a reaction in 1×buffer comprising 100 mM Tris-Cl, pH7.0, 150 mM KCl, 10 mM MgCl2, 5% PEG, and [E]=20 nM using cloned pre-tRNA$^{phe}$ as a substrate;

*Staphylococcus aureus* RNaseP $k_{cat}$=3.4±0.1 min$^{-1}$ determined in a reaction in 1×buffer comprising 100 mM Tris-Cl, pH7.0, 150 mM KCl, 10 mM MgCl2, 5% PEG, and [E]=20 nM using cloned pre-tRNA$^{phe}$ as a substrate;

*Staphylococcus aureus* RNaseP RNA binding isotherm of $K_d$=8±1 nM for RNaseP protein determined in a reaction buffer comprising 20 mM K-Hepes, pH8.0, 0.01% NP-40, 400 mM NH$_4$OAc, 10 mM MgCl$_2$, and 5% glycererol;

*Staphylococcus aureus* RNaseP V1 cleavage of nucleotides selected from the group consisting of: 8–11, 16–23, 30–33, 37–54, 64–84, 96–105, 119–130, 150–156, 166–169, 181–184, and 290–294; and

*Staphylococcus aureus* RNase T2 cleavage of nucleotides selected from the group consisting of: 24–27, 55–60, 86–91, 106–108, 135–138, and 170–177; and said compound modulates the DEPC cleavage of nucleotides selected from the group consisting of: 159–161, A211–213.A203, 204, and A169, 292–294 (L15.2), 271 (bulged A).

2. An antagonist that inhibits an activity of a polypeptide selected from the group consisting of: an RNA transcribed from a polynucleotide comprising an nucleotide sequence having at least a 90% identity to the amino acid sequence of SEQ ID NO:3, and an RNA transcribed from a polynucleotide comprising an nucleotide sequence set forth in SEQ ID NO:3, wherein said activity is selected from the group consisting of:

*Staphylococcus aureus* RNaseP $K_m$=53±4 nM determined in a reaction in 1×buffer comprising 100 mM Tris-Cl, pH7.0, 150 mM KCl, 10 mM MgCl2, 5% PEG, and [E]=20 nM using cloned pre-tRNA$^{phe}$ a substrate;

*Staphylococcus aureus* RNaseP $k_{cat}$=3.4±0.1 min$^{-1}$ determined in a reaction in 1×buffer comprising 100 mM Tris-Cl, pH7.0, 150 mM KCl, 10 mM MgCl2, 5% PEG, and [E]=20 nM using cloned pre-tRNA$^{phe}$ as a substrate;

*Staphylococcus aureus* RNaseP RNA binding isotherm of $K_d$=8±1 nM for RNaseP protein determined in a reaction buffer comprising 20 mM K-Hepes, pH8.0, 0.01% NP-40, 400 mM NH$_4$OAc, 10 mM MgCl$_2$, and 5% glycererol;

*Staphylococcus aureus* RNaseP V 1 cleavage of nucleotides selected from the group consisting of: 8–11, 16–23, 30–33, 37–54, 64–84, 96–105, 119–130, 150–156, 166–169, 181–184, and 290–294; and Staphylococcus aureus RNase T2 cleavage of nucleotides selected from the group consisting of: 24–27, 55–60, 86–91, 106–108, 135–138, and 170–177; and said compound modulates the DEPC cleavage of nucleotides selected from the group consisting of: 159–161, A211–213.A203, 204, and A169, 292–294 (L15.2), 271(bulged A).

* * * * *